United States Patent
Oda et al.

[11] Patent Number: 5,840,652
[45] Date of Patent: Nov. 24, 1998

[54] SULFONYL COMPOUND AND THERMALSENSITIVE RECORDING MEDIUM USING THE SAME

[75] Inventors: Shigeru Oda; Eiji Kawabata, both of Osaka, Japan

[73] Assignee: Sanko Kaihatsu Kagaku Kenkyusho, Ibaraki, Japan

[21] Appl. No.: 801,255

[22] Filed: Feb. 19, 1997

[30] Foreign Application Priority Data

Feb. 21, 1996 [JP] Japan ..................... 8-033508

[51] Int. Cl.$^6$ ..................... B41M 5/30
[52] U.S. Cl. ............ 503/216; 427/150; 503/204
[58] Field of Search ................... 427/150, 151; 503/216, 217, 225, 204

[56] References Cited

U.S. PATENT DOCUMENTS 3,539,375  11/1970  Baum ....................... 503/217

FOREIGN PATENT DOCUMENTS

| | | | |
|---|---|---|---|
| 131 631 A1 | 1/1985 | European Pat. Off. | 503/216 |
| 466 096 A1 | 1/1992 | European Pat. Off. | 503/216 |
| 567 314 A1 | 10/1993 | European Pat. Off. | 503/216 |
| 706 997 A1 | 4/1996 | European Pat. Off. | 503/216 |
| 3-54655 | 3/1991 | Japan | 503/216 |
| 7-247319 | 9/1995 | Japan | 428/500 |

OTHER PUBLICATIONS

Communication dated Sep. 4, 1997, European Search Report (and Annex) No. EP 97 10 2653.

*Primary Examiner*—Bruce H. Hess
*Attorney, Agent, or Firm*—Kane, Dalsimer, Sullivan, Kurucz, Levy, Eisele and Richard, LLP

[57] ABSTRACT

There is provided a developer composition including at least one of sulfonyl compounds represented by formula (1) and at least one of sulfonyl compounds represented by formula 2:

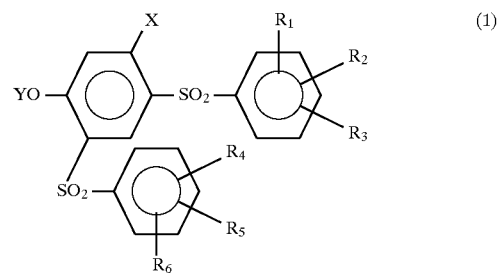

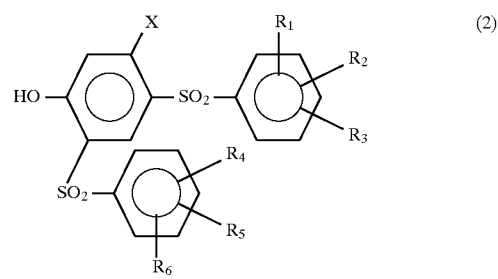

wherein X is H or lower alkyl, $R_1$, $R_2$, $R_3$, $R_4$, $R_5$ and $R_6$ which may be the same or different, present H, halogen or lower alkyl and Y represents alkyl, benzenesulfonyl, benzoyl et al, A thermalsensitive recording medium having the above developer is of high sensitivity, less surface-blushing with lapse of time and is excellent in storage stability of a recorded image, particularly in heat resistance, humidity resistance and anti-plasticizer.

2 Claims, 15 Drawing Sheets

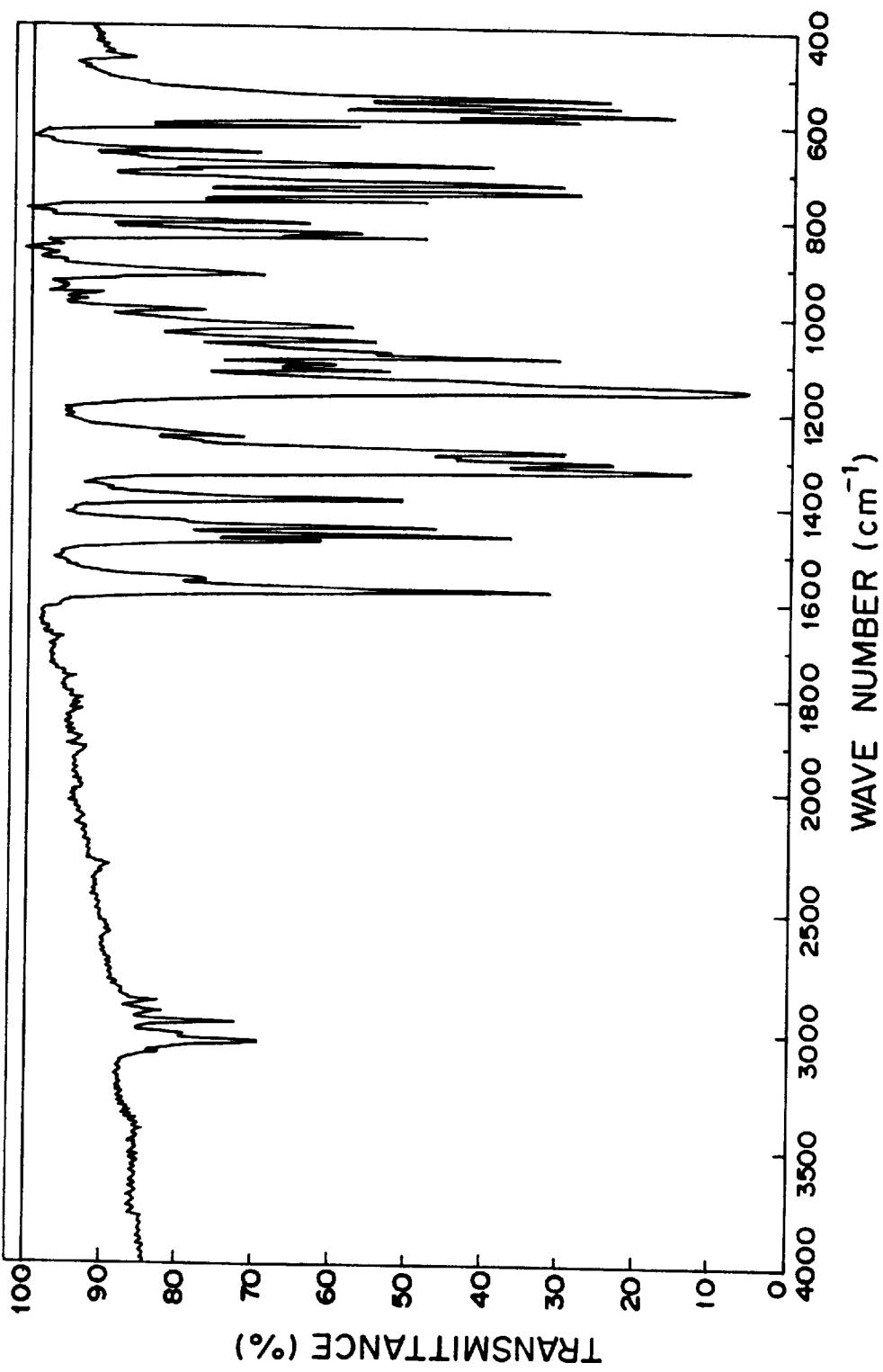
F I G. 10

SULFONYL COMPOUND AND THERMALSENSITIVE RECORDING MEDIUM USING THE SAME

BACKGROUND OF THE INVENTION

1. Field of the Invention

The present invention relates to a specific sulfonyl compound and the use of said compound, and more particularly, in case said compound coexists with a specific developer for thermalsensitive recording medium, an aqueous slurry of developer has a good stability against hydration with lapse of time and the sensitive recording medium is high sensitive, less surface blushing and has the storage stability of recorded image, more particularly excellent in moisture resistance, heat resistance and anti-plasticizer.

2. Prior Art

A thermosensible recording medium has been well known in the art, which uses the thermal-coloring reaction of an electron-donative basic dye precursor and an electron-acceptive developer. Among others, 2,2-bis(4-hydroxyphenyl) propane and 4-hydroxy-4'-isoproxy-diphenylsulfone are well known as the developer (For example, Japanese Patent KOKOKU No.3-54655, etc.).

However, regarding a thermosensible recording medium to which said developer is applied, further improvements of the storage stability for color development, in particular, the moisture resistance, the heat, resistance and anti-plasticizer have been required. In order to solve these problems, the present inventors previously found a compound having the following formula (2):

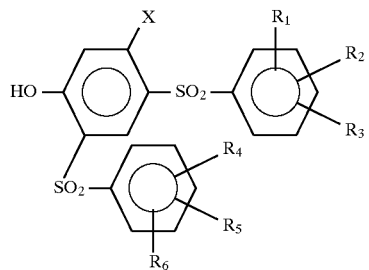

wherein X represents hydrogen atom or an alkyl group of 1~4 carbon atoms; $R_1$, $R_2$, $R_3$, $R_4$, $R_5$ and $R_6$ are identical with one another or different from one another, and each of them represents hydrogen atom, a halogen atom or an alkyl group of 1~4 carbon atoms, and filed a patent application [Kokai Koho (Publication) No. JP-A-7-247319] on said compound. However, thereafter it was found that a thermalsensitive recording medium to which said compound is applied as a developer is excellent in the above subject matter, however, when an aqueous slurry of said developer was conserved at 40° C., a deterioration of dispersion due to hydration occurs, and then, the thermalsensitive recording medium to which said compound was applied causes a surface-blushing of the supporting base at 60° C. which should be improved.

SUMMARY OF THE INVENTION

It is an object of the present invention to provide a sulfonyl compound used for a thermalsensible recording medium, which is highly sensitive and less surface blushing and also, has a good storage property of recorded image, particularly recording properties excellent in the moisture resistance, heat resistance and anti-plasticizer, namely, the sulfonyl compound capable of preventing the developer aqueous slurry of the above general formula (2) from the deterioration of dispersion due to hydration so that the stability of dispersion with lapse of time can be improved.

The inventor have diligently studied to obtain the thermalsensitive recording medium of high sensitivity and having a good storage property of recorded image by preventing the developer slurry of the above general formula (2) from the deterioration of dispersion due to hydration and as a result, have found a sulfonyl compound represented by general formula (1),

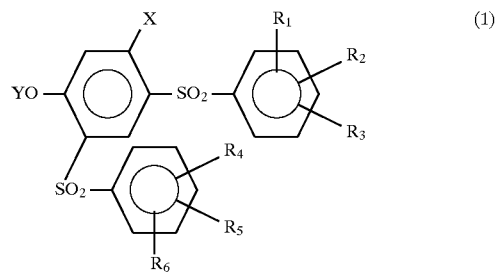

wherein each of X stands for a hydrogen atom or an alkyl group of 1~4 carbon atoms; $R_1$, $R_2$, $R_3$, $R_4$, $R_5$ and $R_6$ which may be the same or different, stand for a hydrogen atom, a halogen atom or an alkyl group of 1~4 carbon atoms, and Y represents alkyl, aralkyl, allyl, cyclohexyl, aryl, alkylaryl, alkylsulfonyl, benzenesulfonyl, alkylbenzenesulfonyl, alkyloyl, benzoyl, alkylbenzoyl, acryloyl, metacryloyl or glycidyl group, and it has been found that the coexistance of the above sulfonyl compound of general formula (1) with the developer represented by the general formula (2) can prevent the hydration of the developer aqueous slurry, whereby the present invention has been accomplished.

BRIEF DESCRIPTION OF THE DRAWINGS

FIG. 10 shows an infrared-absorption spectrogram of the compound obtained in Working Example 10;

DETAILED DESCRIPTION OF THE INVENTION

Figure 1:
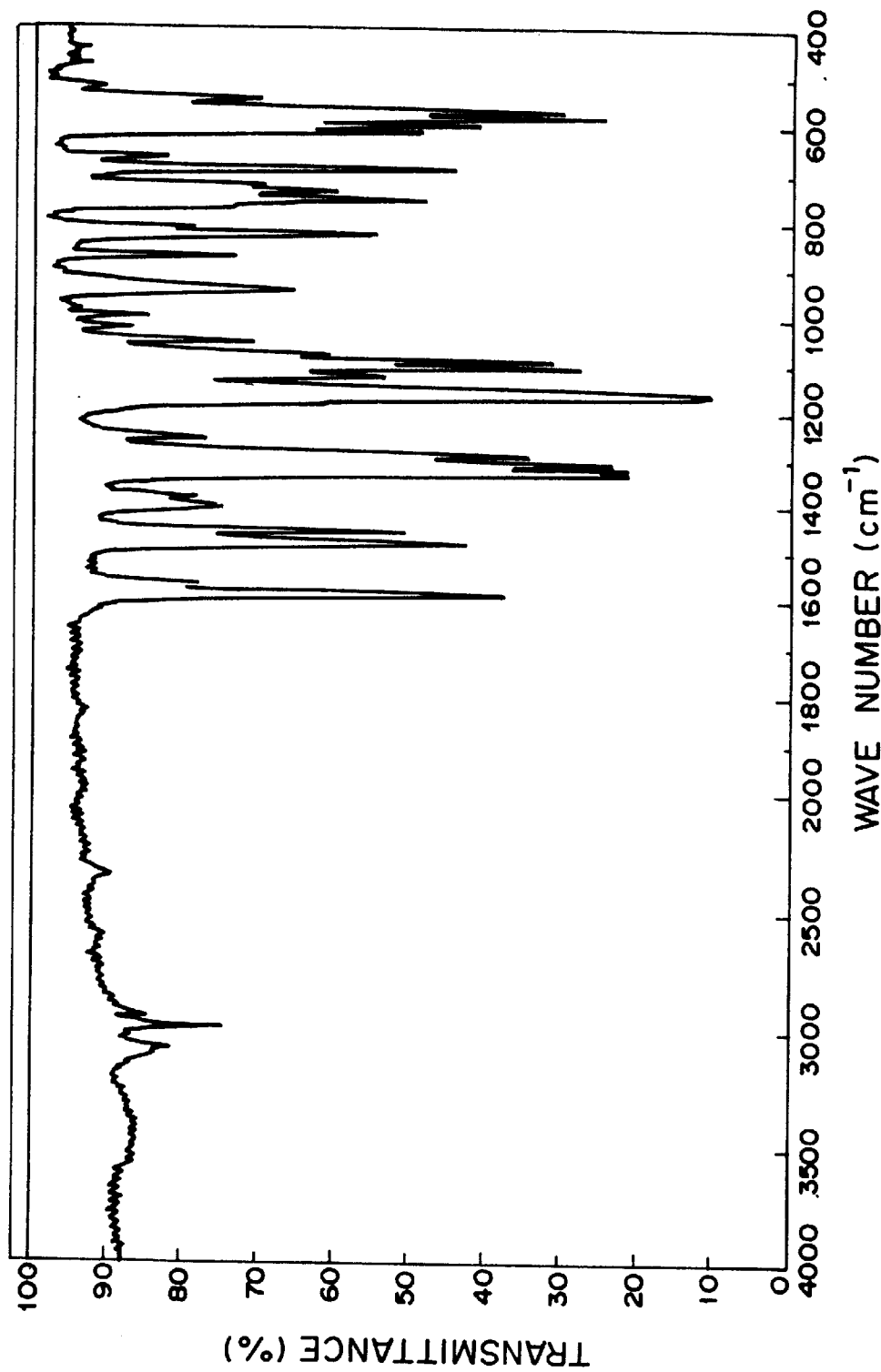
FIG. 1 shows an infrared-absorption spectrogram of the compound obtained in Working Example 1.

The compounds represented by general formula (1) relating to the present invention will be in detail explained. The definitions of X, Y, $R_1$, $R_2$, $R_3$, $R_4$, $R_5$ and $R_6$ are as mentioned above. As for Y, there are preferably exemplified an alkyl group of 1~6 carbon atoms, an aralkyl group of 1~4 carbon atoms, an allyl group, a cyclohexyl group, an aryl group substituted by an alkyl group of 1~12 carbon atoms, an aryl group, an alkylsulfonyl group of 1~18 carbon atoms, a benzenesulfonyl group, an alkyl group of 1~12 carbon atoms-substituted benzenesulfonyl group, an alkyloyl of 1~18 carbon atoms, a benzoyl group, an alkylbenzoyl group of 1~6 carbon atoms, an acryloyl group, a metacryloyl group and a glycidyl group.

The following compounds can be cited as concrete examples of compounds represented by the general formula (1):

(1) 1-methoxy-2,4-bis(phenylsulfonyl)benzene;
(2) 1-ethoxy-2,4-bis(phenylsulfonyl)benzene;
(3) 1-n-propoxy-2,4-bis(phenylsulfonyl)benzene;
(4) 1-iso-propoxy-2,4-bis(phenylsulfonyl)benzene;
(5) 1-n-butoxy-2,4-bis(phenylsulfonyl)benzene;
(6) 1-sec-butoxy-2,4-bis(phenylsulfonyl)benzene;
(7) {2,4-bis(phenylsulfonyl)phenyl} benzyl ether;
(8) {2,4-bis(phenylsulfonyl)phenyl} allyl ether;
(9) {2,4-bis(phenylsulfonyl)phenyl} phenyl ether;
(10) {2,4-bis(phenylsulfonyl)phenyl} methanesulfonate;
(11) {2,4-bis(phenylsulfonyl)phenyl} benzenesulfonate;
(12) {2,4-bis(phenylsulfonyl)phenyl} 4-methylbenzenesulfonate;
(13) {2,4-bis(phenylsulfonyl)phenyl} 2,4-dimethylbenzenesulfonate;
(14) {2,4-bis(phenylsulfonyl)phenyl} 2,5-dimethylbenzenesulfonate;
(15) {2,4-bis(phenylsulfonyl)phenyl} 3,4-dimethylbenzenesulfonate;
(16) {2,4-bis(phenylsulfonyl)phenyl} acetate;
(17) 1-stearoyloxy-2,4-bis(phenylsulfonyl)benzene;
(18) {2,4-bis(phenylsulfonyl)phenyl} phenylcarboxylate;
(19) {2,4-bis(phenylsulfonyl)phenyl} 4-methylphenylcarboxylate;
(20) {2,4-bis(phenylsulfonyl)phenyl} acrylate;
(21) {2,4-bis(phenylsulfonyl)phenyl} methacrylate;
(22) 1-{2,4-bis(phenylsulfonyl)phenoxy}-2,3-epoxypropane;
(23) {2,4-bis(phenylsulfonyl)phenoxy} n-hexyl ether;
(24) {2,4-bis(phenylsulfonyl)phenoxy} stearyl ether;
(25) {2,4-bis(phenylsulfonyl)phenoxy} cyclohexyl ether;
(26) 1-iso-propoxy-2,4-bis(4-methylphenylsulfonyl)benzene;
(27) 1-methoxy-2,4-bis(4-methylphenylsulfonyl)benzene;
(28) {2,4-bis(4-methylphenylsulfonyl)phenyl} allyl ether;
(29) {2,4-bis(4-methylphenylsulfonyl)phenyl}-benzenesulfonate;
(30) {2,4-bis(4-methylphenylsulfonyl)phenyl} 4-methylbenzenesulfonate;
(31) {2,4-bis(4-methylphenylsulfonyl)phenyl} acetate;
(32) {2,4-bis(4-methylphenylsulfonyl)phenyl}-phenylcarboxylate;
(33) {2,4-bis(4-methylphenylsulfonyl)phenyl} acrylate;
(34) 1-{2,4-bis(4-methylphenylsulfonyl)phenoxy}-2,3-epoxypropane;
(35) 1-iso-propoxy-2,4-bis(2,5-dimethylphenylsulfonyl)benzene;
(36) 1-methoxy-2,4-bis(2,5-dimethylphenylsulfonyl)benzene;
(37) {2,4-bis(2,5-dimethylphenylsulfonyl)phenyl} allyl ether;
(38) {2,4-bis(2,5-dimethylphenylsulfonyl)phenyl}-benzenesulfonate;
(39) {2,4-bis(2,5-dimethylphenylsulfonyl)phenyl} 2,5-dimethylbenzenesulfonate;
(40) {2,4-bis(2,5-dimethylphenylsulfonyl)phenyl} acetate;
(41) {2,4-bis(2,5-dimethylphenylsulfonyl)phenyl}-phenylcarboxylate;
(42) {2,4-bis(2,5-dimethylphenylsulfonyl)phenyl} acrylate;
(43) 1-{2,4-bis (2,5-dimethylphenylsulfonyl)phenoxy}-2,3-epoxypropane;
(44) 1-iso-propoxy-2,4-bis(phenylsulfonyl)-5-methylbenzene;
(45) 1-ethoxy-2,4-bis(phenylsulfonyl)-5-methylbenzene;
(46) {2,4-bis(phenylsulfonyl)-5-methylphenyl} allyl ether;
(47) {2,4-bis(phenylsulfonyl)-5-methylphenyl}-benzenesulfonate;
(48) {2,4-bis(phenylsulfonyl)-5-methylphenyl} acetate;
(49) {2,4-bis(phenylsulfonyl)-5-methylphenyl}-phenylcarboxylate;
(50) {2,4-bis(phenylsulfonyl)-5-methylphenyl} acrylate;
(51) 1-{2,4-bis (phenylsulfonyl)-5-methylphenoxy}-2,3-epoxypropane;
(52) 1-iso-propoxy-2,4-bis(phenylsulfonyl)-5-ethylbenzene;
(53) 1-ethoxy-2,4-bis(phenylsulfonyl)-5-ethylbenzene;
(54) {2,4-bis(phenylsulfonyl)-5-ethylphenyl} allyl ether;
(55) {2,4-bis(phenylsulfonyl)-5-ethylphenyl} benzenesulfonate;
(56) {2,4-bis(phenylsulfonyl)-5-ethylphenyl} acetate;
(57) {2,4-bis(phenylsulfonyl)-5-ethylphenyl}-phenylcarboxylate;
(58) {2,4-bis(phenylsulfonyl)-5-ethylphenyl} acrylate;
(59) 1-{2,4-bis(phenylsulfonyl)-5-ethylphenoxy}-2,3-epoxypropane;
(60) {1-iso-propoxy-2-(4-methylphenylsulfonyl)-4-phenylsulfonyl} benzene;
(61) {2-(4-methylphenylsulfonyl)-4-(phenylsulfonyl)-phenyl} allyl ether;
(62) {2-(4-methylphenylsulfonyl)-4-(phenylsulfonyl)-phenyl} benzenesulfonate;
(63) {2-(4-methylphenylsulfonyl)-4-(phenylsulfonyl)-phenyl} phenylcarboxylate;
(64) {1-methoxy-2-(4-methylphenylsulfonyl)-4-phenylsulfonyl} benzene;
(65) {1-iso-propoxy-2-(2,5-dimethylphenylsulfonyl)-4-phenylsulfonyl} benzene;
(66) {2-(2,5-dimethylphenylsulfonyl)-4-(phenylsulfonyl)-phenyl} benzenesulfonate;
(67) {2-(2,5-dimethylphenylsulfonyl)-4-(phenylsulfonyl)-phenyl} phenylcarboxylate;
(68) {1-methoxy-2-(2,5-dimethylphenylsulfonyl)-4-phenylsulfonyl} benzene;
(69) 1-iso-propoxy-2,4-bis(3,4-dimethylphenylsulfonyl)-benzene;
(70) {2,4-bis(3,4-dimethylphenylsulfonyl)phenyl} allyl ether;
(71) {2,4-bis(3,4-dimethylphenylsulfonyl)phenyl}-benzenesulfonate;
(72) {2,4-bis(3,4-dimethylphenylsulfonyl)phenyl} 3,4-dimethylbenzenesulfonate;
(73) {2,4-bis(3,4-dimethylphenylsulfonyl)phenyl}-phenylcarboxylate;
(74) 1-methoxy-2,4-bis(3,4-dimethylphenylsulfonyl) benzene;

(75) 1-iso-propoxy-2,4-bis(4-chlorophenylsulfonyl)benzene;
(76) {2,4-bis(4-chlorophenylsulfonyl)phenyl} allyl ether;
(77) {2,4-bis(4-chlorophenylsulfonyl)phenyl}-benzenesulfonate;
(78) {2,4-bis(4-chlorophenylsulfonyl)phenyl} 4-chlorobenzenesulfonate;
(79) {2,4-bis(4-chlorophenylsulfonyl)phenyl}-phenylcarboxylate; or
(80) 1-ethoxy-2,4-bis(4-chlorophenylsulfonyl)benzene.

Next, a method of peparing sulfonyl compounds presented by the general formula (1) will be describd, which can be shown by the following formula:

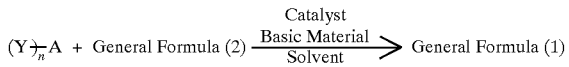

wherein "n" is 1 or 2 ; when "n" is 1 , "Y" has the same meaning as "Y" in the general formula (1), and "A" is chlorine or bromine atom; and when "n" is 2, "Y" is methoxy or ethoxy group, and "A" is sulfonyl group.

As a catalyst of the present reaction, potassium iodine, zinc chloride, feric chloride, aluminum chloride, magnesium chloride, triethylbenzyl ammonium, or the like is preferred, and as a basic material, sodium carbonate, potassium carbonate, sodium hydroxide, potassium hydroxide, triethylamine, pyridine or the like is preferred.

Next, the following compounds can be cited as concrete examples of compounds which are represented by the general formula (2); an aqueous slurry of the above compounds being hydrated by itself, while the coexistence of a compound represented by the general formula (1) with one represented by the general formula (2) effectively acts so as to prevent the hydration of an aqueous slurry of the developer whereby providing the thermalsensitive recording medium having excellent properties:

(81) 2,4-bis(phenylsulfonyl)phenyl;
(82) 2,4-bis(2-methylphenylsulfonyl)phenol;
(83) 2,4-bis(4-methylphenylsulfonyl)phenol;
(84) 2,4-bis(4-bromophenylsulfonyl)phenol;
(85) 2,4-bis(4-chrolophenylsulfonyl)phenol;
(86) 2,4-bis(2,4-dimethylphenylsulfonyl)phenol;
(87) 2,4-bis(3,4-dimethylphenylsulfonyl)phenol;
(88) 2,4-bis(2,5-dimethylphenylsulfonyl)phenol;
(89) 2,4-bis(2,4,6-trimethylphenylsulfonyl)phenol;
(90) 2,4-bis(4-ethylphenylsulfonyl)phenol;
(91) 2,4-bis(4-iso-propylphenylsulfonyl)phenol;
(92) 2,4-bis(phenylsulfonyl)-5-methylphenol;
(93) 2,4-bis(2-methylphenylsulfonyl)-5-methylphenol;
(94) 2,4-bis(4-methylphenylsulfonyl)-5-methylphenol;
(95) 2,4-bis(4-iso-propylphenylsulfonyl)-5-methylphenol;
(96) 2,4-bis(2,4-dimethylphenylsulfonyl)-5-methylphenol;
(97) 2,4-bis(2,5-dimethylphenylsulfonyl)-5-methylphenol;
(98) 2,4-bis(phenylsulfonyl)-5-ethylphenol;
(99) 2,4-bis(4-methylphenylsulfonyl)-5-ethylphenol;
(100) 2,4-bis(4-ethylphenylsulfonyl)-5-ethylphenol;
(101) 2,4-bis(2,4-dimethylphenylsulfonyl)-5-ethylphenol;
(102) 2,4-bis(2,5-dimethylphenylsulfonyl)-5-ethylphenol;
(103) 2,4-bis(phenylsulfonyl)-5-iso-propylphenol;
(104) 2-(4-methylphenylsulfonyl)-4-(phenylsulfonyl)phenol;
(105) 2-(4-ethylphenylsulfonyl)-4-(phenylsulfonyl)phenol;
(106) 2-(4-iso-propylphenylsulfonyl)-4-(phenylsulfonyl)phenol;
(107) 2-(2,5-dimethylphenylsulfonyl)-4-(phenylsulfonyl)phenol;
(108) 2-(2,4-dimethylphenylsulfonyl)-4-(phenylsulfonyl)phenol;
(109) 2-(3,4-dimethylphenylsulfonyl)-4-(phenylsulfonyl)phenol;
(110) 2-(4-chrolophenylsulfonyl)-4-(phenylsulfonyl)phenol;
(111) 2-(4-bromophenylsulfonyl)-4-(phenylsulfonyl)phenol;
(112) 2-(phenylsulfonyl)-4-(4-methylphenylsulfonyl)phenol;
(113) 2-(phenylsulfonyl)-4-(4ethylphenylsulfonyl)phenol;
(114) 2-(phenylsulfonyl)-4-(4-iso-propylphenylsulfonyl)phenol;
(115) 2-(phenylsulfonyl)-4-(2-methylphenylsulfonyl)phenol;
(116) 2-(phenylsulfonyl)-4-(2,5-dimethylphenylsulfonyl)phenol;
(117) 2-(phenylsulfonyl)-4-(2,4-dimethylphenylsulfonyl)phenol;
(118) 2-(phenylsulfonyl)-4-(3,4-dimethylphenylsulfonyl)phenol;
(119) 2-(phenylsulfonyl)-4-(4-chlorophenylsulfonyl)phenol;
(120) 2-(phenylsulfonyl)-4-(4-bromophenylsulfonyl)phenol;
(121) 2-(4-methylphenylsulfonyl)-4-(phenylsulfonyl)-5-methylphenol;
(122) 2-(4-chlorophenylsulfonyl)-4-(phenylsulfonyl)-5-methylphenol;
(123) 2-(4-bromophenylsulfonyl)-4-(phenylsulfonyl)-5-methylphenol;
(124) 2-(phenylsulfonyl)-4-(4-methylphenylsulfonyl)-5-methylphenol;
(125) 2-(phenylsulfonyl)-4-(4-chrolophenylsulfonyl)-5-methylphenol;
(126) 2-(phenylsulfonyl)-4-(4-bromophenylsulfonyl)-5-methylphenol;
(127) 2-(4-methylphenylsulfonyl)-4-(phenylsulfonyl)-5-ethylphenol;
(128) 2-(4-chrolophenylsulfonyl)-4-(phenylsulfonyl)-5-ethylphenol;
(129) 2-(4-bromophenylsulfonyl)-4-(phenylsulfonyl)-5-ethylphenol;
(130) 2-(phenylsulfonyl)-4-(4-methylphenylsulfonyl)-5-ethylphenol;
(131) 2-(phenylsulfonyl)-4-(4-chrolophenylsulfonyl)-5-ethylphenol;
(132) 2-(phenylsulfonyl)-4-(4-bromophenylsulfonyl)-5-ethylphenol;
(133) 2-(4-methylphenylsulfonyl)-4-(phenylsulfonyl)-5-iso-propylphenol; or
(134) 2-(phenylsulfonyl)-4-(4-methylphenylsulfonyl)-5-iso-propylphenol.

When the compound represented by the general formula (1) is used together with one represented by the general formula (2), preferable compounds represented by the general formulas (1) and (2), each of which is shown by the compound number thereof, can be cited as follows:
 the general formula (1):
  (1)–(27), (29), (30), (32), (35), (36), (38), (39), (41), (44), (45), (47), (49), (52), (53), (55), (60)–(75), (77) and (78); and
 the general formula (2):
  (81), (83), (85)–(88), (90)–(92), (94), (95), (99)–(105), (107)–(110), (112)–(119), (121), (124), (127) and 130).

More preferable compounds represented by the general formulas (1) and (2) are as follows:
 the general formula (1):
  (1)–(27), (30), (35), (36), (39), (44), (45), (47), (52), (53), (55), (60)–(75) and (78);

the general formula (2):

(81), (83), (85)–(88), (92), (104), (107)–(1 10), (112), (116)–(119), (121) and (124).

Incidentally, two or more of compounds represented by the general formulas (1) may coexist with two or more of compounds represented by the general formulas (2).

Furthermore, the amount of compounds represented by the general formula (1) used is too small relative to the amount of compounds of the general formula (2), the effect is lost, however, a too large amount thereof causes economical disadvantages. Therefore, the amount of the compound represented by the general formula (1) relative to that of the general formula (2) is preferably in the range of from about 10 ppm to about twofold by weight, more preferably in the range of from about 20 ppm to about equivalent by weight.

Furthermore, as a method of compounding and preparing, any one of the following methods can be used: (a) a method of in a desired ratio mixing and preparing a pulverized compound (s) of formula (1) and a pulverized compound (s) of formula (2); (b) a method of incorporating a compound (s) of formula (1) with a compound (s) of formula (2) in a desired ratio, mixing and pulverizing them; (c) a method of incorporating a preliminarly pulverized compound (s) of formula (1) with a non-pulverized compound (s) of formula (2) in a desired ratio, mixing and pulverizing them; and (d) a method of pulverizing compounds of formulas (1) and (2), which were preliminarily mixed and prepared in a desired ratio by a recrystallizing method or a mix melting method.

Furthermore, the total amount to be used of this composition as a developer is 50–600 parts by weight relative to 100 parts by weight of a basic dye, preferably 100–400 parts by weight, on the basis of conversion to the compound of formula (2).

Next, a basic dye and a sensitizing agent which are used for a recording medium of the present invention will be described.

As a basic dye, a triarylmethane system compound, a diarylmethane type compound, pyridine type compound, a spiro type compound, a Rhodamine-lactam type compound, a fluoran type compound, an indolylphthalide type compound, a fluorene type compound or the like is exemplified. Among others, 3-N,N-dibutylamino-6-methyl-7-anilinofluoran, 3-N,N-diethylamino-6-methyl-7-anilinofluoran, 3-(N-isopentyl-N-ethyl)-6-methyl-7-anilinofluoran, 3-(N-cyclohexyl-N-methyl)-6-methyl-7-anilinofluoran, 3-N,N-diethyl-6-chloro-7-anilinofluoran, Crystal Violet lactone or the like is exemplified as a typical basic dye. These dyes may be used alone or in mixture thereby providing an adjustment of color tone of colored image and a multi-color thermalsensitive recording medium.

Next, as the sensitizing agent, a nitrogen containing compound, an ester compound, a hydrocarbon compound, an ether compound, sulfone compound or the like is exemplified. Among others, β-naphtylbenzyl ether, stearamide, 4-benzyloxybenzyl benzoate ester, dibenzyl oxalate, di-p-methylbenzyl oxalate, bis(4-methylphenyl)carbonate, 4-benzylbiphenyl, m-terphenyl, 1,2-bis(3-methylphenoxy)ethane, 1,2-bis(phenoxy)ethane, diphenyl sulfone, 3,3',4,4'-tetramethyl-diphenylethane or the like is typically exemprified. Such a sensitizing agent may be used alone or in combination of two or more. Furthermore, the amount of the sensitizing agent used to 100 parts by weight of the basic dye is in the range of 50–800 parts by weight, preferably 100–400 parts by weight.

Incidentally, as a method of pulverizing the sensitizing agent, any method of the following (a)–(c) may be used: (a) a method of pulverizing the sensitizing agent by itself; (b) a method of mixing the sensitizing agent and the dye in a desired ratio to pulverize them; and (c) a method of mixing the sensitizing agent and a composition comprising a compound of formula (1) and a compound of formula (2) so as to pulverize them.

A thermalsensitive recording medium of the present invention can be produced according to a conventional meshed, and it is unnecessary to use a special method. For example, a basic dye, a developer, a sensitizing agent, a pigment, a metal soap, a wax and the like can be pulverized to a particle size of usually up to 5 $\mu$m, preferably up to 1.5 $\mu$m, and dispersed in an aqueous medium containing a surface active agent, an antifoaming agent, a dispersing agent and the like by using a means such as a ball mil or sand mil so as to prepare a coating liquid.

As a pigment as mentioned above, calcium carbonate, magnesium carbonate, titanium oxide, kaolin, silica, amorphous silica, zinc oxide and the like are exemplified.

As a metal soap, zinc strearate, calcium stearate, aluminum stearate and the like are exemprified.

As a wax, a paraffin wax, a microcrystalline wax, polyethylene wax and the like are exemplified.

As a surface active agent, an alkaline metallic salt of a sulfosuccinate, an alkaline metallic salt of an alkylbenzenesulfonate, a sodium salt of a lauryl alcohol sulfate ester and the like are exemplified. As a dispersing agent, sodium polyacrylate, poly (vinyl alcohol) responding to various saponification degrees, pH and polymerization degrees, carboxymethyl cellulose, hydroxyethyl cellulose, polyacrylamide, starch and the like are exemplified.

A thermalsensitive recording layer of the thermmalsensitive recording medium of the present invention can be formed according to the known methods, which are not limited to a specific one. For example, a coating liquid for the thermalsensitive recording layer can be applied onto the surface of a base material by using a suitable coating apparatus such as an air knife coater, a blader coater, a bar coater, a rod coater, gravure coater, curtain coater, a wire bar or the like so as to dry and form the thermalsensitive recording layer. The amount of the coating liquid applied is not restricted in particular, which is generally applied on the surface of the base material in an amount of 0.5 to 50 gr./m$^3$, preferably 1.0 to 20 gr./m$^3$ by dry weight. As the base material, paper sheets, a plastic sheet, a synthetic paper or the like are used.

Working Examples:

The present invention will be explained through working examples as follows:

(Working Example 1)

93.5 gr. of 2,4-bis(phenylsulfonyl)phenol, 12 gr. of sodium hydroxide, 0.5 gr. of potassium iodide, 200 ml of isopropyl alcohol and 100 ml of water were fed into a reactor having a volume of 1 liter, and were heated to a temperature of 70° C. in an atmosphere of nitrogen gas so as to be dissolved while stirring. At the same temperature, 24 gr. of isopropyl chloride was dropped over ten hours. After the dropping was finished, the solution was digested at the temperature for a period of ten hours, and thereafter, 300 ml of water was added thereto, and deposited crystallines were filtered, and the crystallines were recrystallized and refined with 300 ml of toluene so as to obtain 85 gr. of white crystalline powders having a melting point of 132° C. From the results of IR-analysis, H-NMR analysis and elemental analysis (see Table 1) thereof, this product was identified as 1-iso-propoxy-2,4-bis(phenylsulfonyl)benzene.

TABLE 1

| Elementary Analysis Values (%) | C | H | S |
|---|---|---|---|
| Found Values | 60.7 | 4.8 | 15.3 |
| Calculated Values (As $C_{21}H_{20}O_5S_2$) | 60.6 | 4.8 | 15.4 |

FIG. 1 shows an infrared-absorption spectrogram thereof according to a potassium bromide disk method (hereinafter the same method is used). Incidentally, in FIGS. 1 to 15, the axis of ordinates shows transmittance (%), while the axis of abscissas shows Wave Number ($cm^{-1}$).

(Working Example 2)

The operation was carried out in the same way as that of Working Example 1, except that 93.5 gr. of 2,4-bis-(phenylsulfonyl)phenol used in Working Example 1 was replaced with 97 gr. of 2,4-bis(phenylsulfonyl)-5-methylphenol. As a result, 88 gr. of white crystalline powders having a melting point of 173° C. were obtained. From the results of IR-analysis, H-NMR analysis and elemental analysis (see Table 2) thereof, this product was identified as 1-iso-propoxy-2,4-bis(phenylsulfonyl)-5-methylbenzene.

TABLE 2

| Elementary Analysis Values (%) | C | H | S |
|---|---|---|---|
| Found Values | 61.3 | 5.1 | 15.0 |
| Calculated Values (As $C_{22}H_{22}O_5S_2$) | 61.4 | 5.2 | 14.9 |

Figure 2:
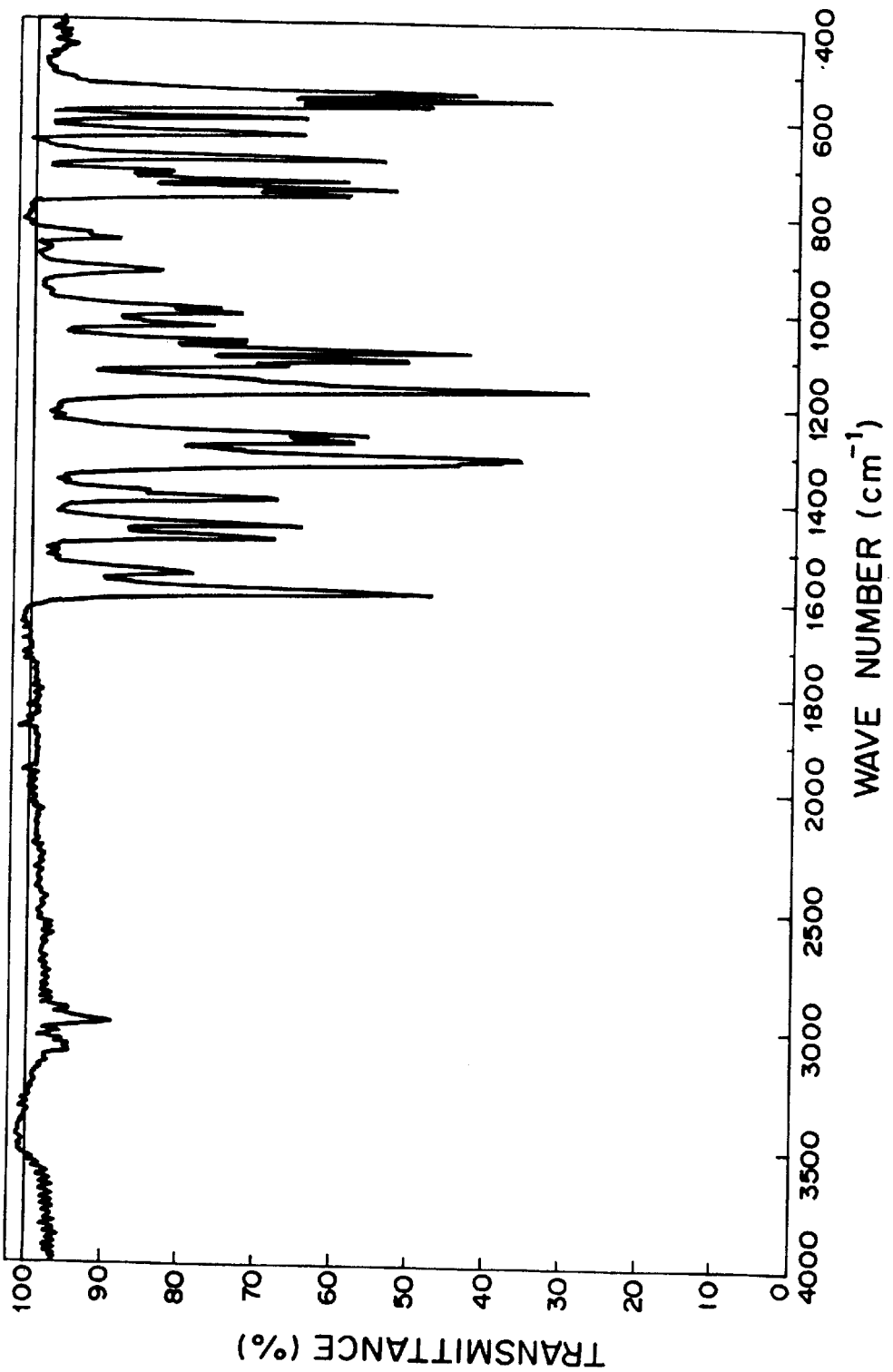
FIG. 2 shows an infrared-absorption spectrogram of the compound obtained in Working Example 2.

FIG. 2 shows an infrared-absorption spectrogram thereof.

(Working Example 3)

93.5 gr. of 2,4-bis(phenylsulfonyl)phenol, 10 gr. of sodium hydroxide and 100 ml of water were fed into a reactor having a volume of 1 liter, and were heated to a temperature of 90° C. in an atmosphere of nitrogen gas so as to be dissolved while stirring. At the same temperature, 40 gr. of dimethylsulfuric acid was dropped over four hours. After the dropping was finished, the solution was digested at the temperature for a period of ten hours, and thereafter, 300 ml of water was added thereto, and deposited crystallines were filtered, and the crystallines were recrystallized and refined with 400 ml of toluene so as to obtain 80 gr. of white crystalline powders having a melting point of 169° C. From the results of IR-analysis, H-NMR analysis and elemental analysis (see Table 3) thereof, this product was identified as 1-methoxy-2,4-bis(phenylsulfonyl)benzene.

TABLE 3

| Elementary Analysis Values (%) | C | H | S |
|---|---|---|---|
| Found Values | 58.8 | 4.1 | 16.6 |
| Calculated Values (As $C_{19}H_{16}O_5S_2$) | 58.7 | 4.2 | 16.5 |

Figure 3:
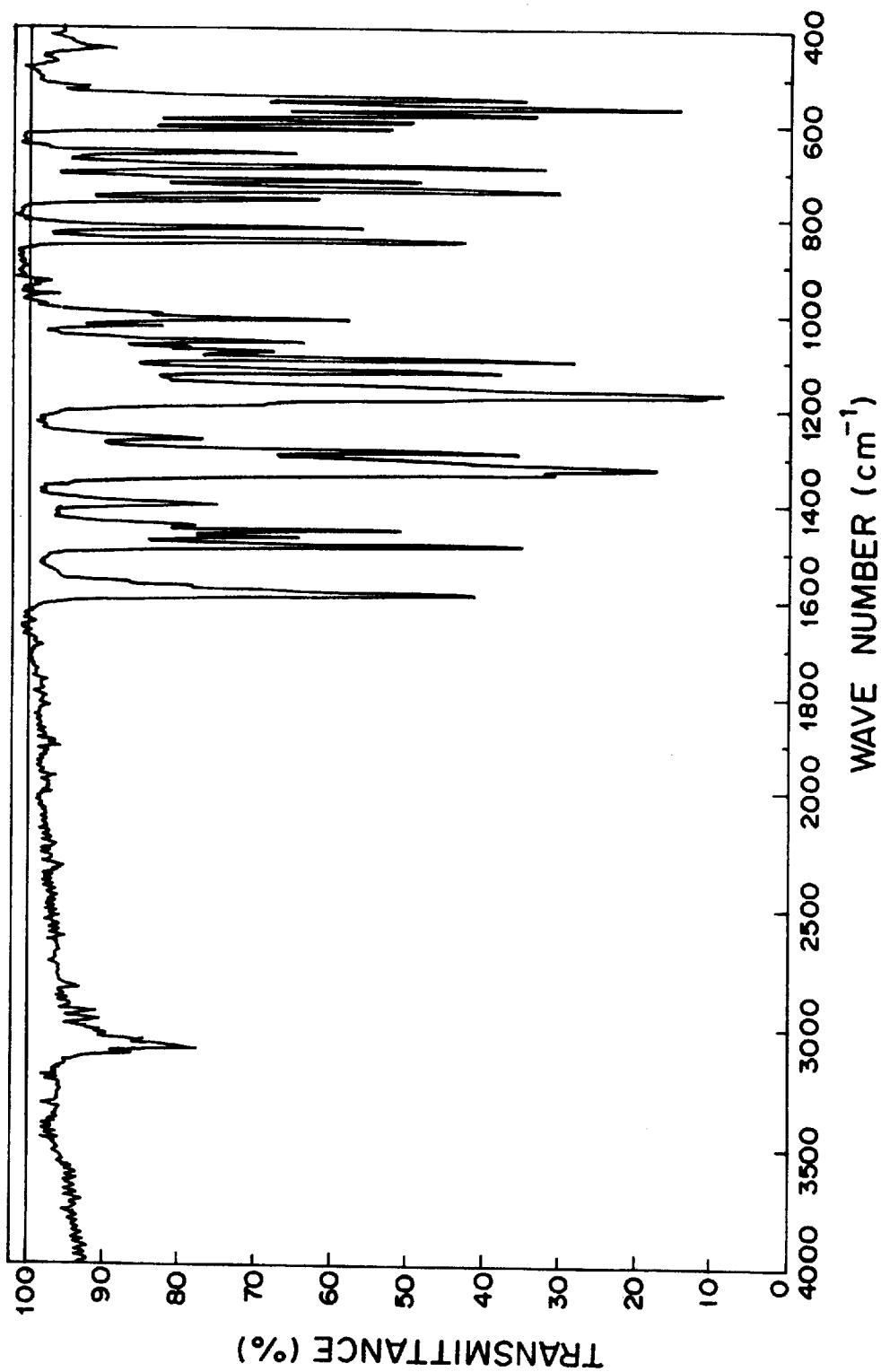
FIG. 3 shows an infrared-absorption spectrogram of the compound obtained in Working Example 3.

FIG. 3 shows an infrared-absorption spectrogram thereof.

(Working Example 4)

The operation was carried out in the same way as that of Working Example 3, except that 93.5 gr. of 2,4-bis-(phenylsulfonyl)phenol used in Working Example 3 was replaced with 97 gr. of 2,4-bis(phenylsulfonyl)-5-methylphenol. As a result, 83 gr. of white crystalline powders having a melting point of 234° C. were obtained. From the results of IR-analysis, H-NMR analysis and elemental analysis (see Table 4) thereof, this product was identified as 1-methoxy-2,4-bis(phenylsulfonyl)-5-methylbenzene.

TABLE 4

| Elementary Analysis Values (%) | C | H | S |
|---|---|---|---|
| Found Values | 59.6 | 4.5 | 16.0 |
| Calculated Values (As $C_{20}H_{18}O_5S_2$) | 59.7 | 4.5 | 15.9 |

Figure 4:
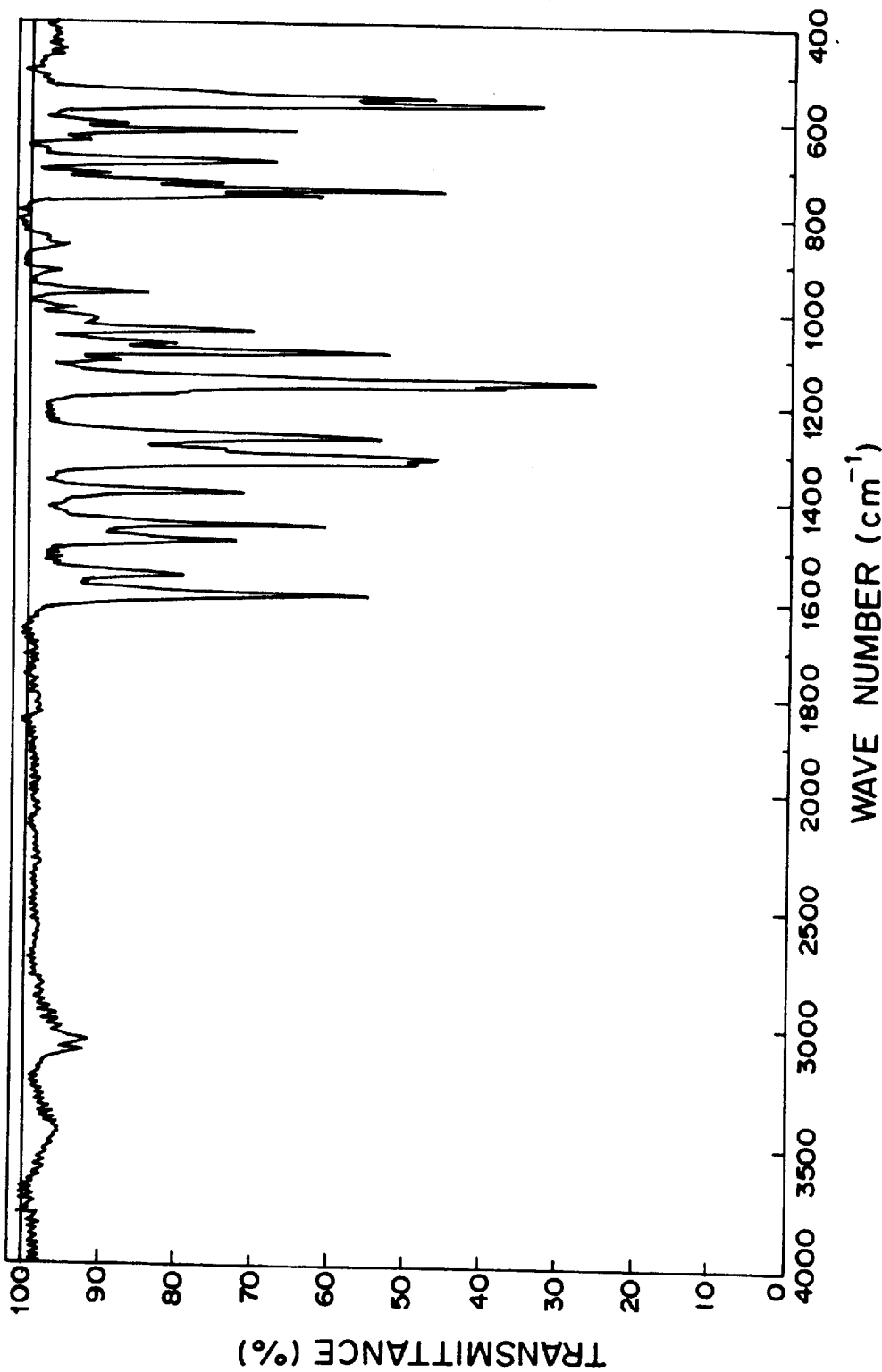
FIG. 4 shows an infrared-absorption spectrogram of the compound obtained in Working Example 4.

FIG. 4 shows an infrared-absorption spectrogram thereof.

(Working Example 5)

93.5 gr. of 2,4-bis(phenylsulfonyl)phenol, 12 gr. of sodium hydroxide, 1 gr. of triethylbenzylammonium chloride and 200 ml of water were fed into a reactor having a volume of 1 liter, and were heated to a temperature of 80° C. in an atmosphere of nitrogen gas so as to be dissolved while stirring. At the same temperature, a mixed liquid of 38 gr. of benzyl chloride and 38 gr. of toluene was dropped over four hours. After the dropping was finished, the solution was digested at the temperature for a period of ten hours, and cooled, and deposited crystallines were filtered, and furthermore, the crystallines were recrystallized and refined with 400 ml of methyl isobutyl ketone so as to obtain 103 gr. of white crystalline powders having a melting point of 181° C. From the results of IR-analysis, H-NMR analysis and elemental analysis (see Table 5) thereof, this product was identified as {2,4-bis(phenylsulfonyl)phenyl} benzyl ether.

TABLE 5

| Elementary Analysis Values (%) | C | H | S |
|---|---|---|---|
| Found Values | 64.5 | 4.4 | 13.9 |
| Calculated Values (As $C_{25}H_{20}O_5S_2$) | 64.6 | 4.3 | 13.8 |

Figure 5:
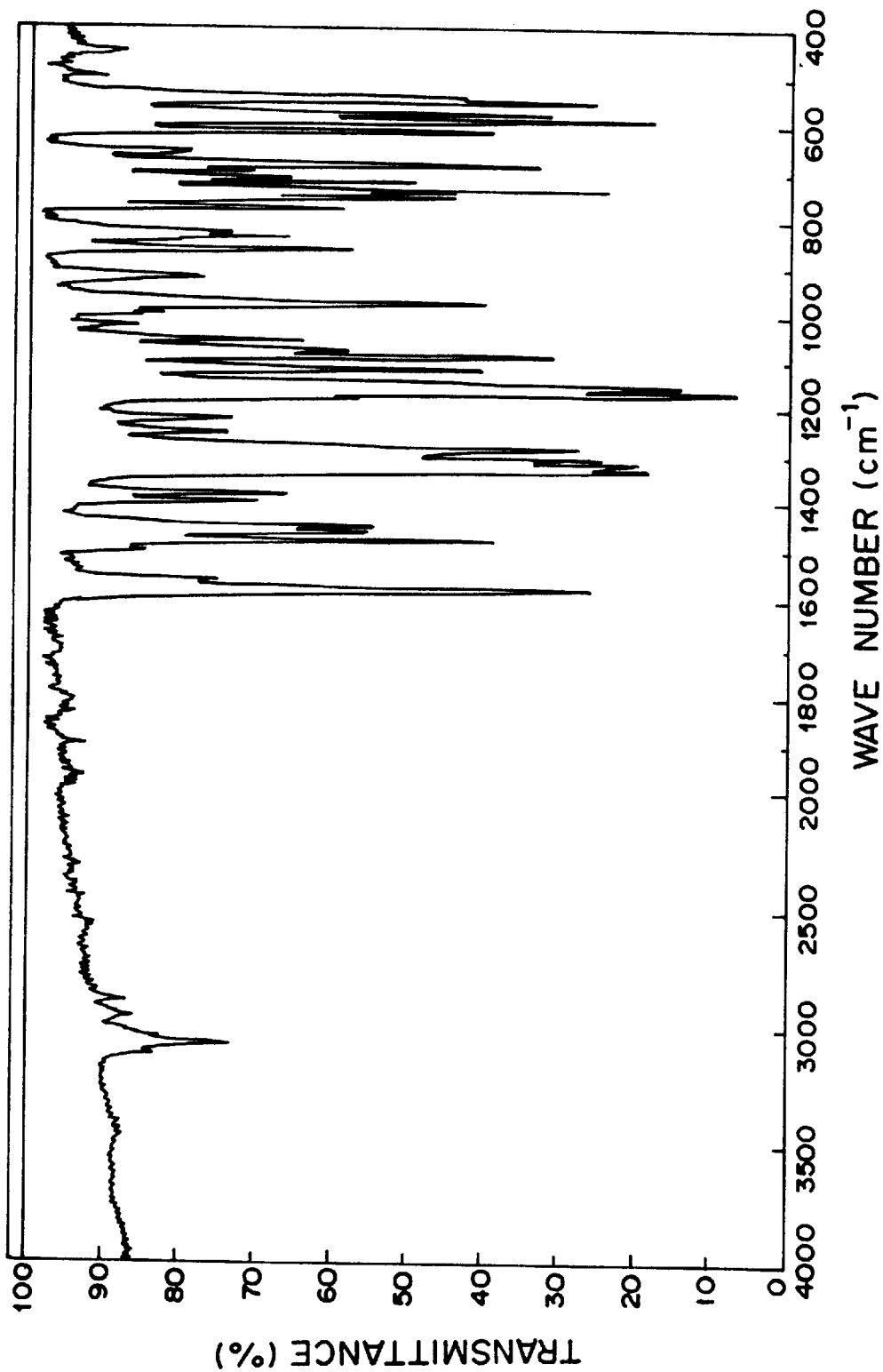
FIG. 5 shows an infrared-absorption spectrogram of the compound obtained in Working Example 5.

FIG. 5 shows an infrared-absorption spectrogram thereof.

(Working Example 6)

93.5 gr. of 2,4-bis(phenylsulfonyl)phenol, 0.1 gr. of zinc chloride and 44.1 gr. of benzenesulfonyl chloride were fed into a reactor having a volume of 1 liter, and were heated to a temperature of 100° C. in an atmosphere of nitrogen gas so as to be dissolved while stirring. The temperature was slowly elevated to 160° C. over ten hours, and thereafter, the dissolved mixture was digested at the temperature for a period of four hours, and cooled to 110° C., and thereafter 300 ml of toluene was added thereto, and 100 ml of water was added thereto so as to water-wash them, and the water layer was separated, and furthermore, 100 ml of water were added thereto so as to water-wash them, and the water layer was separated, and thereafter, the oil content was subjected to an azeotropic dewatering. The resulting product was refined by a recrystallization method so as to obtain 116 gr. of white crystalline powders having a melting point of 146° C. From the results of IR-analysis, H-NMR analysis and elemental analysis (see Table 6) thereof, this product was identified as {2,4-bis(phenylsulfonyl)phenyl} benzenesulfonate.

TABLE 6

| Elementary Analysis Values (%) | C | H | S |
|---|---|---|---|
| Found Values | 56.1 | 3.5 | 18.5 |
| Calculated Values (As $C_{24}H_{18}O_7S_3$) | 56.0 | 3.5 | 18.7 |

Figure 6:
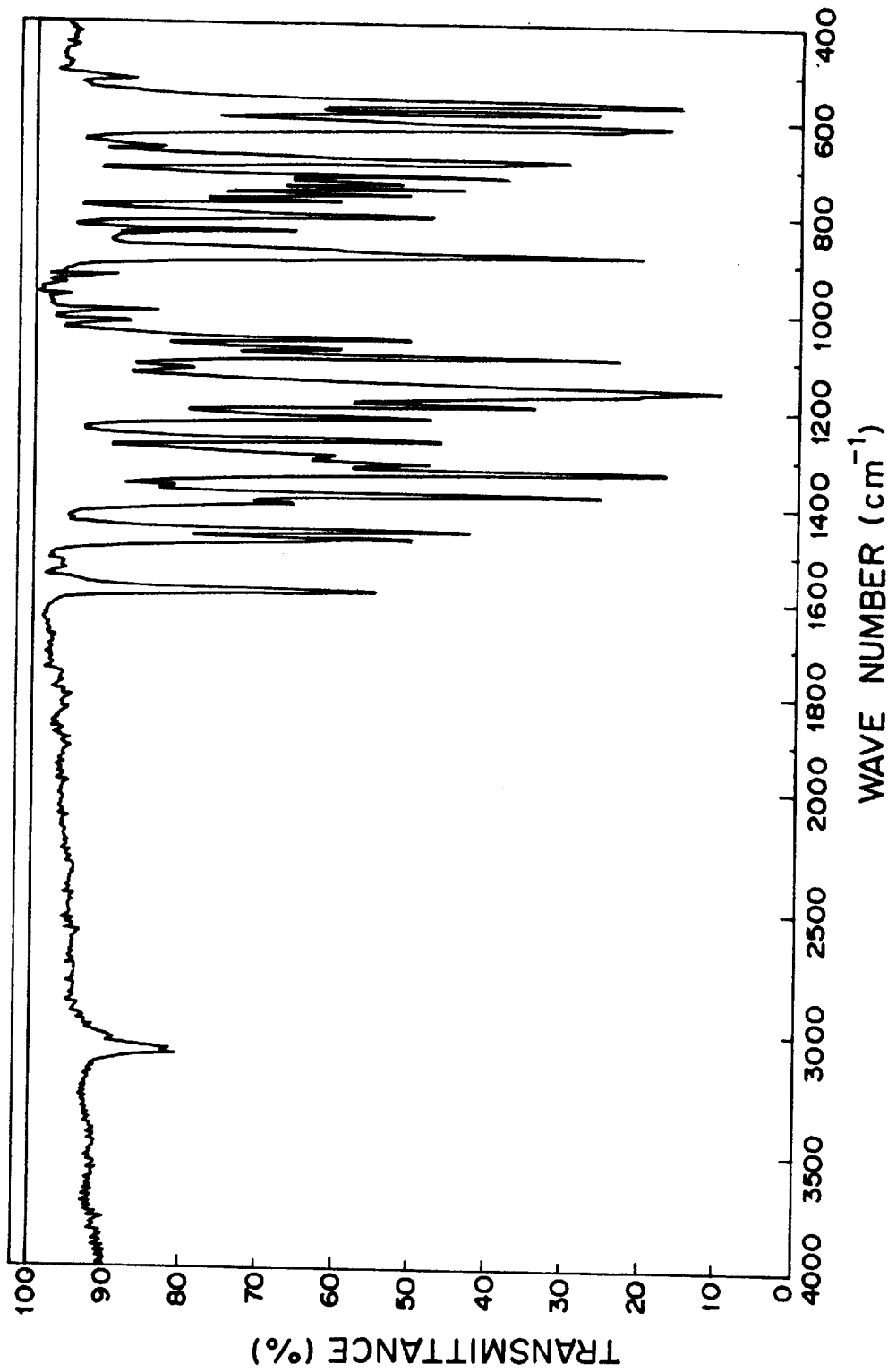
FIG. 6 shows an infrared-absorption spectrogram of the compound obtained in Working Example 6.

FIG. 6 shows an infrared-absorption spectrogram thereof.

(Working Example 7)

The operation was carried out in the same way as that of Working Example 6, except that 93.5 gr. of 2,4-bis- (phenylsulfonyl)phenol used in Working Example 6 was replaced with 97 gr. of 2,4-bis(phenylsulfonyl)-5-methylphenol. As a result, 121 gr. of white crystalline powders having a melting point of 163° C. were obtained. From the results of IR-analysis, H-NMR analysis and elemental analysis (see Table 7) thereof, this product was identified as {2,4-bis-(phenylsulfonyl)-5-methylphenyl} benzenesulfonate.

TABLE 7

| Elementary Analysis Values (%) | C | H | S |
| --- | --- | --- | --- |
| Found Values | 56.7 | 3.8 | 18.2 |
| Calculated Values (As $C_{25}H_{20}O_7S_3$) | 56.8 | 3.8 | 18.2 |

Figure 7:
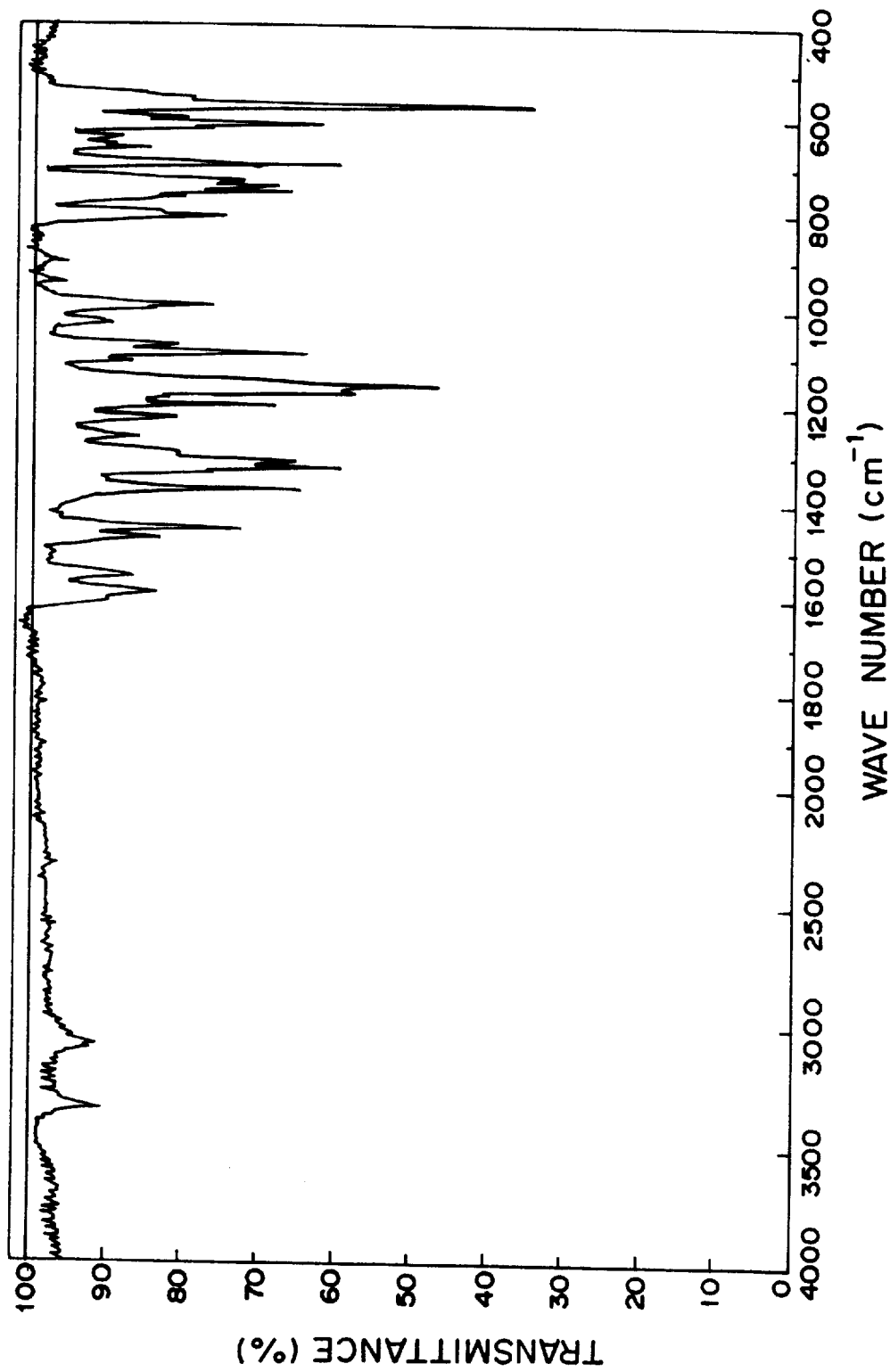
FIG. 7 shows an infrared-absorption spectrogram of the compound obtained in Working Example 7.

FIG. 7 shows an infrared-absorption spectrogram thereof.

(Working Example 8)

The operation was carried out in the same way as that of Working Example 6, except that 93.5 gr. of 2,4-bis-(phenylsulfonyl)phenol and 44.1 gr. of benzenesulfonyl chloride used in Working Example 6 were replaced with 107.5 gr. of 2,4-(2,5-dimethylphenylsulfonyl)phenol and 51.1 gr. of 2,5-dimethylbenzenesulfonyl chloride, respectively. As a result, 121 gr. of white crystalline powders having a melting point of 157° C. were obtained. From the results of IR-analysis, H-NMR analysis and elemental analysis (see Table 8) thereof, this product was identified as {2,4-bis(2,5-dimethylbenzenesulfonyl)phenyl} 2,5-dimethylbenzenesulfonate.

TABLE 8

| Elementary Analysis Values (%) | C | H | S |
| --- | --- | --- | --- |
| Found Values | 60.2 | 5.0 | 15.8 |
| Calculated Values (As $C_{30}H_{30}O_7S_3$) | 60.2 | 5.1 | 16.1 |

Figure 8:
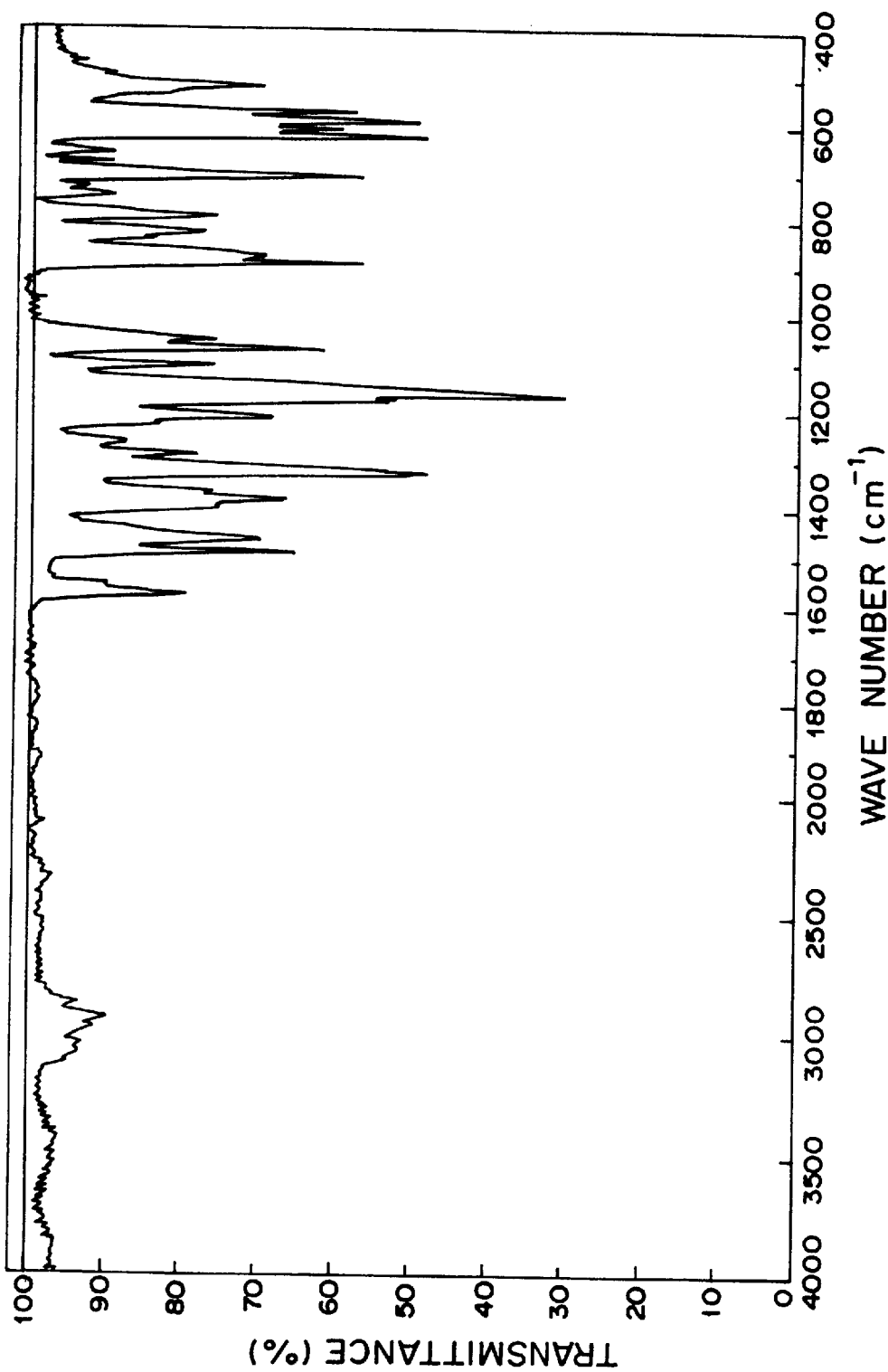
FIG. 8 shows an infrared-absorption spectrogram of the compound obtained in Working Example 8.

FIG. 8 shows an infrared-absorption spectrogram thereof.

(Working Example 9)

The operation was carried out in the same way as that of Working Example 6, except that 93.5 gr. of 2,4-bis-(phenylsulfonyl)phenol and 44.1 gr. of benzenesulfonyl chloride used in Working Example 6 were replaced with 107.5 gr. of 2,4-(3,4-dimethylphenylsulfonyl)phenol and 51.1 gr. of 3,4-dimethylbenzenesulfonyl chloride, respectively. As a result, 115 gr. of white crystalline powders having a melting point of 223° C. were obtained. From the results of IR-analysis, H-NMR analysis and elemental analysis (see Table 9) thereof, this product was identified as {2,4-bis(3,4-dimethylbenzenesulfonyl)phenyl} 3,4-dimethylbenzenesulfonate.

TABLE 9

| Elementary Analysis Values (%) | C | H | S |
| --- | --- | --- | --- |
| Found Values | 60.0 | 5.0 | 16.1 |
| Calculated Values (As $C_{30}H_{30}O_7S_3$) | 60.2 | 5.1 | 16.1 |

Figure 9:
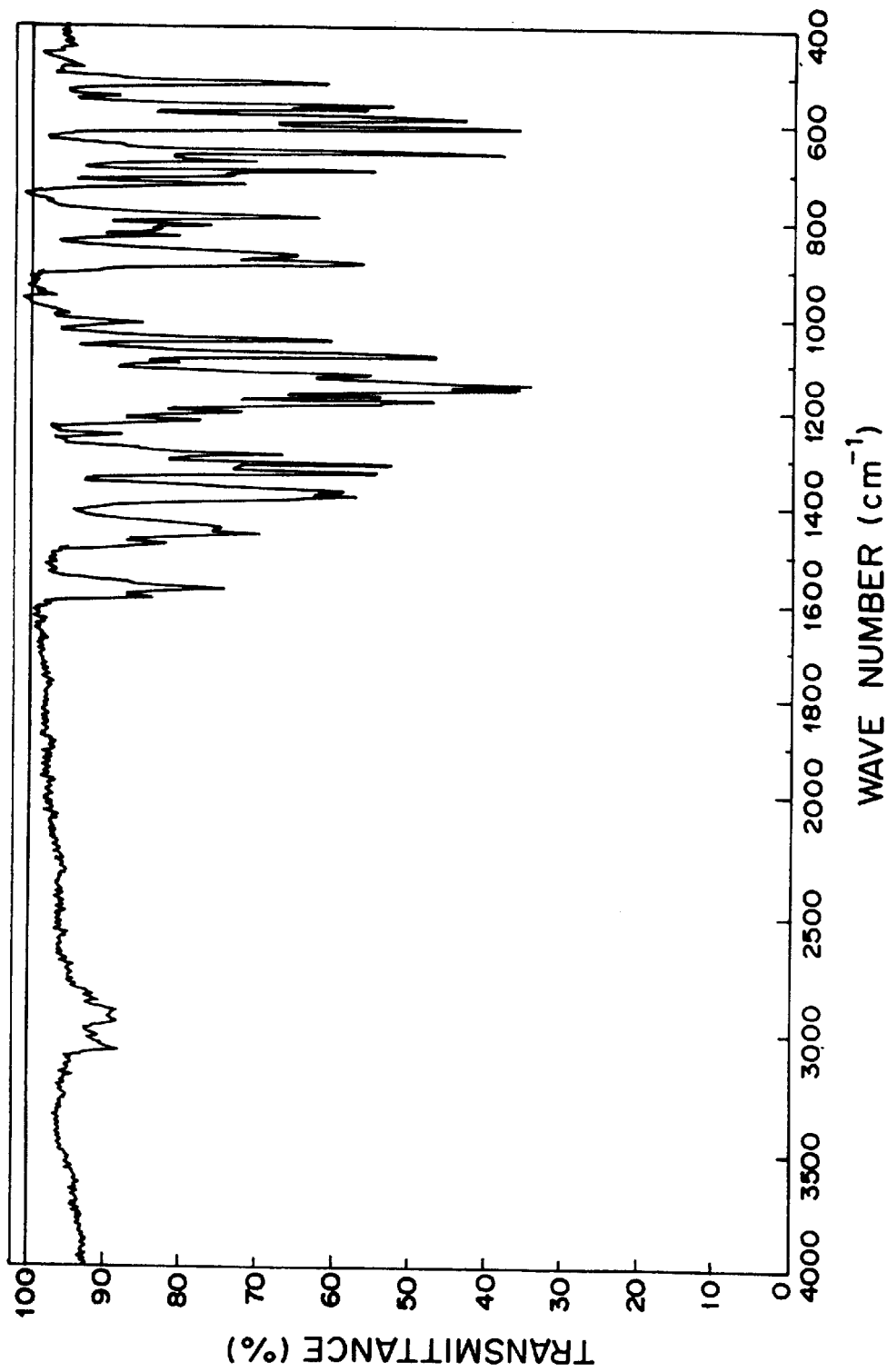
FIG. 9 shows an infrared-absorption spectrogram of the compound obtained in Working Example 9.

FIG. 9 shows an infrared-absorption spectrogram thereof.

(Working Example 10)

The operation was carried out in the same way as that of Working Example 3, except that 40 gr. of dimethylsulfuric acid and 400 ml of toluene as a recrystallizing solvent used in Working Example 3 were replaced with 50 gr. of diethylsulfuric acid and (300 ml: 100 ml) of (toluene: methyl isobutyl ketone). As a result, 90 gr. of white crystalline powders having a melting point of 193° C. were obtained. From the results of IR-analysis, H-NMR analysis and elemental analysis (see Table 10) thereof, this product was identified as 1-ethoxy-2,4-bis(phenylsulfonyl)benzene.

TABLE 10

| Elementary Analysis Values (%) | C | H | S |
| --- | --- | --- | --- |
| Found Values | 59.0 | 4.4 | 16.0 |
| Calculated Values (As $C_{20}H_{18}O_5S_2$) | 59.1 | 4.5 | 15.9 |

FIG. 10 shows an infrared-absorption spectrogram thereof.

(Working Example 11)

The operation was carried out in the same way as that of Working Example 5, except that 38 gr. of benzylchoride, 400 ml of methyl isobutyl ketone as a recrystallizing solvent, and furthermore, the reaction temperature of 80° C. used in Working Example 5 were replaced with 36 gr. of allyl bromide, 400 ml of toluene and 60° C., respectively. As a result, 85 gr. of white crystalline powders having a melting point of 168° C. were obtained. From the results of IR-analysis, H-NMR analysis and elemental analysis (see Table 11)thereof, this product was identified as {2,4-bis(phenylsulfonyl)phenyle} allyl ether.

TABLE 11

| Elementary Analysis Values (%) | C | H | S |
| --- | --- | --- | --- |
| Found Values | 60.8 | 4.4 | 15.4 |
| Calculated Values (As $C_{21}H_{18}O_5S_2$) | 60.9 | 4.4 | 15.5 |

Figure 11:
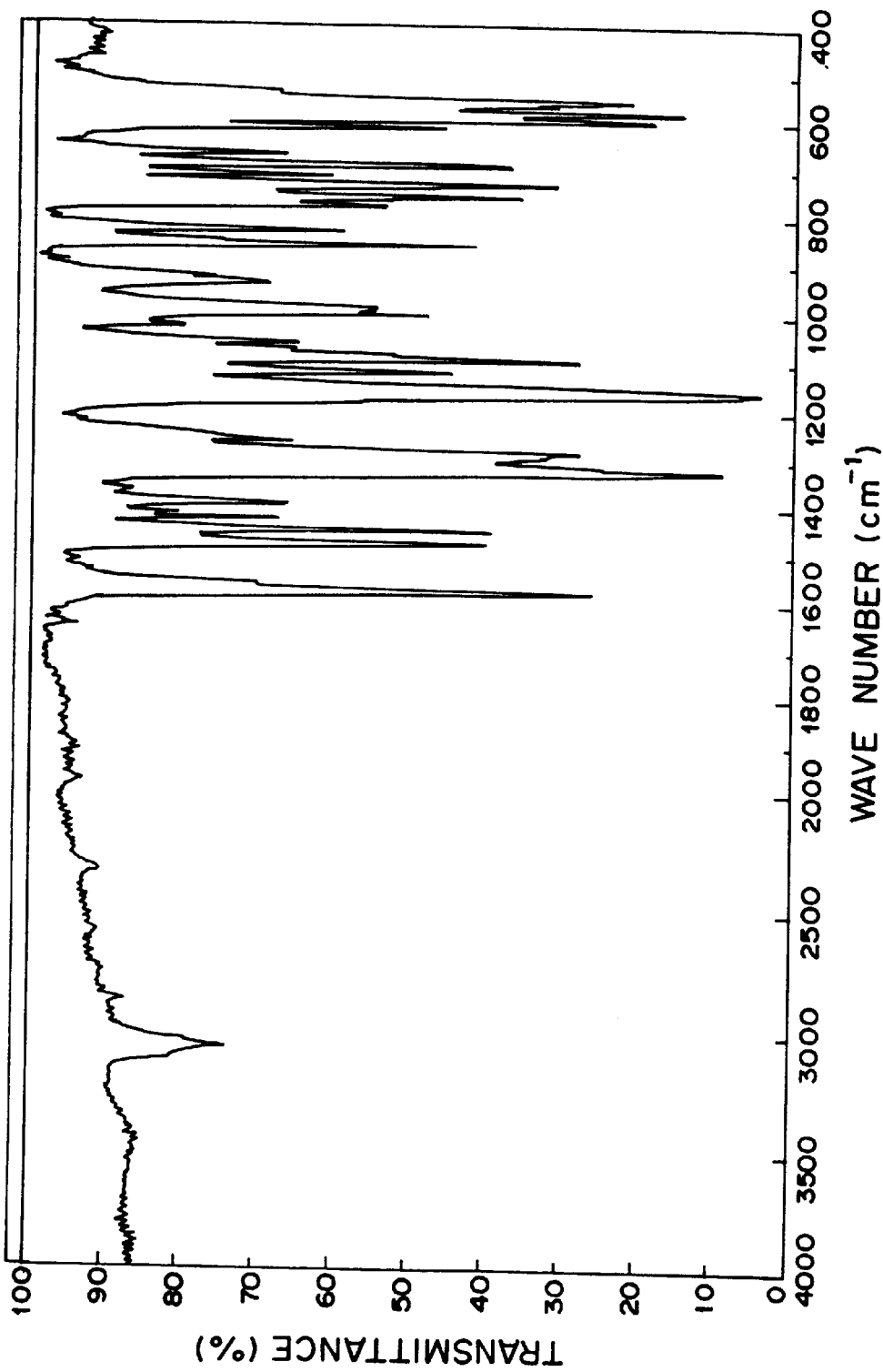
FIG. 11 shows an infrared-absorption spectrogram of the compound obtained in Working Example 11.

FIG. 11 shows an infrared-absorption spectrogram thereof.

(Working Example 12)

The operation was carried out in the same way as that of Working Example 1, except that 24 gr. of isopropyl chloride and 300 ml of toluene as a recrystallizing solvent used in Working Example 1 were replaced with 50 gr. of n-hexane bromide and 300 ml of ethanol, respectively. As a result, 90 gr. of white crystalline powders having a melting point of 115° C. were obtained. From the results of IR-analysis, H-NMR analysis and elemental analysis (see Table 12) thereof, this product was identified as {2,4-bis(phenylsulfonyl)phenyl} n-hexyl ether.

TABLE 12

| Elementary Analysis Values (%) | C | H | S |
| --- | --- | --- | --- |
| Found Values | 63.0 | 5.6 | 13.8 |
| Calculated Values (As $C_{24}H_{26}O_5S_2$) | 62.9 | 5.7 | 14.0 |

Figure 12:
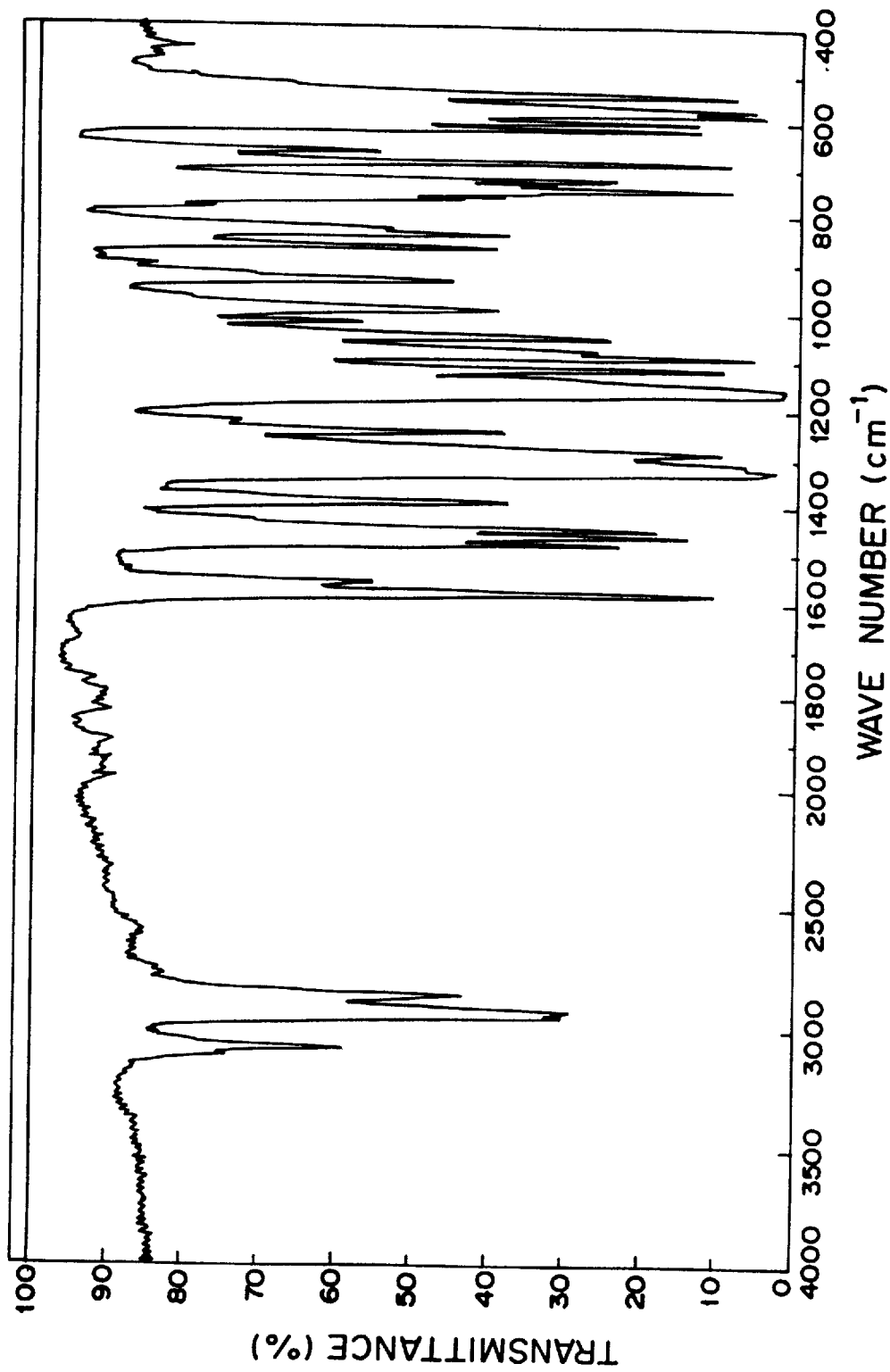
FIG. 12 shows an infrared-absorption spectrogram of the compound obtained in Working Example 12.

FIG. 12 shows an infrared-absorption spectrogram thereof.

(Working Example 13)

93.5 gr. of 2,4-bis(phenylsulfonyl)phenol, 34 gr. of pyridine and 300 ml of toluene were fed into a reactor having a volume of 1 liter, and were heated to a temperature of 60° C. in an atmosphere of nitrogen gas, while stirring. At the same temperature, 42.1 gr. of benzoyl chloride was dropped over two hours. After the dropping was finished, the solution was digested at the temperature for a period of five hours, and thereafter, an aqueous dilute hydrochloric acid of 5% was added thereto, the mixture was agitated and water-washed. After allowing it to stand, a lower water-layer was separated, and furthermore, after adding 100 ml of water, the same operation was carried out. The oil content was subjected to an azeotropic dewatering, and recrystallized and refined so as to obtain 95 gr. of white crystalline powders having a melting point of 141° C. From the results of IR-analysis, H-NMR analysis and elemental analysis (see Table 13) thereof, this product was identified as {2,4-bis-(phenylsulfonyl)phenyl} phenylcarboxylate.

TABLE 13

| Elementary Analysis Values (%) | C | H | S |
|---|---|---|---|
| Found Values | 62.7 | 3.7 | 13.5 |
| Calculated Values (As $C_{25}H_{18}O_6S_2$) | 62.8 | 3.8 | 13.4 |

Figure 13:
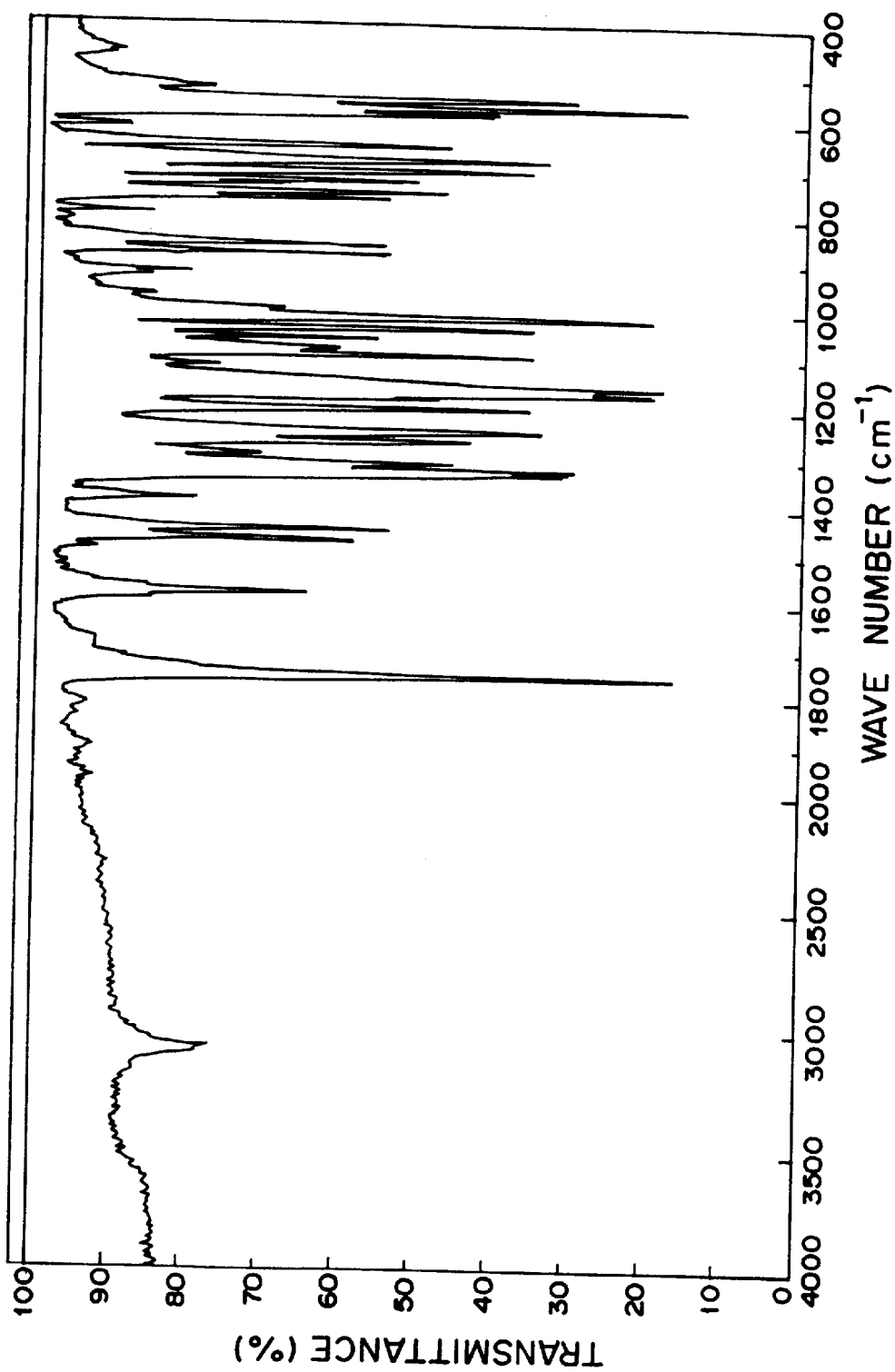
FIG. 13 shows an infrared-absorption spectrogram of the compound obtained in Working Example 13.

FIG. 13 shows an infrared-absorption spectrogram thereof.

(Working Example 14)

The operation was carried out in the same way as that of Working Example 13, except that 42.1 gr. of benzoyl chloride used in Working Example 13 was replaced with 93.5 gr. of stearoyl chloride. As a result, 120 gr. of white crystalline powders having a melting point of 82° C. were obtained. From the results of IR-analysis, H-NMR analysis and elemental analysis (see Table 14) thereof, this product was identified as 1-stearoyloxy-2,4-bis(phenylsulfonyl)benzene.

TABLE 14

| Elementary Analysis Values (%) | C | H | S |
|---|---|---|---|
| Found Values | 67.4 | 7.4 | 10.1 |
| Calculated Values (As $C_{36}H_{48}O_6S_2$) | 67.5 | 7.5 | 10.0 |

Figure 14:
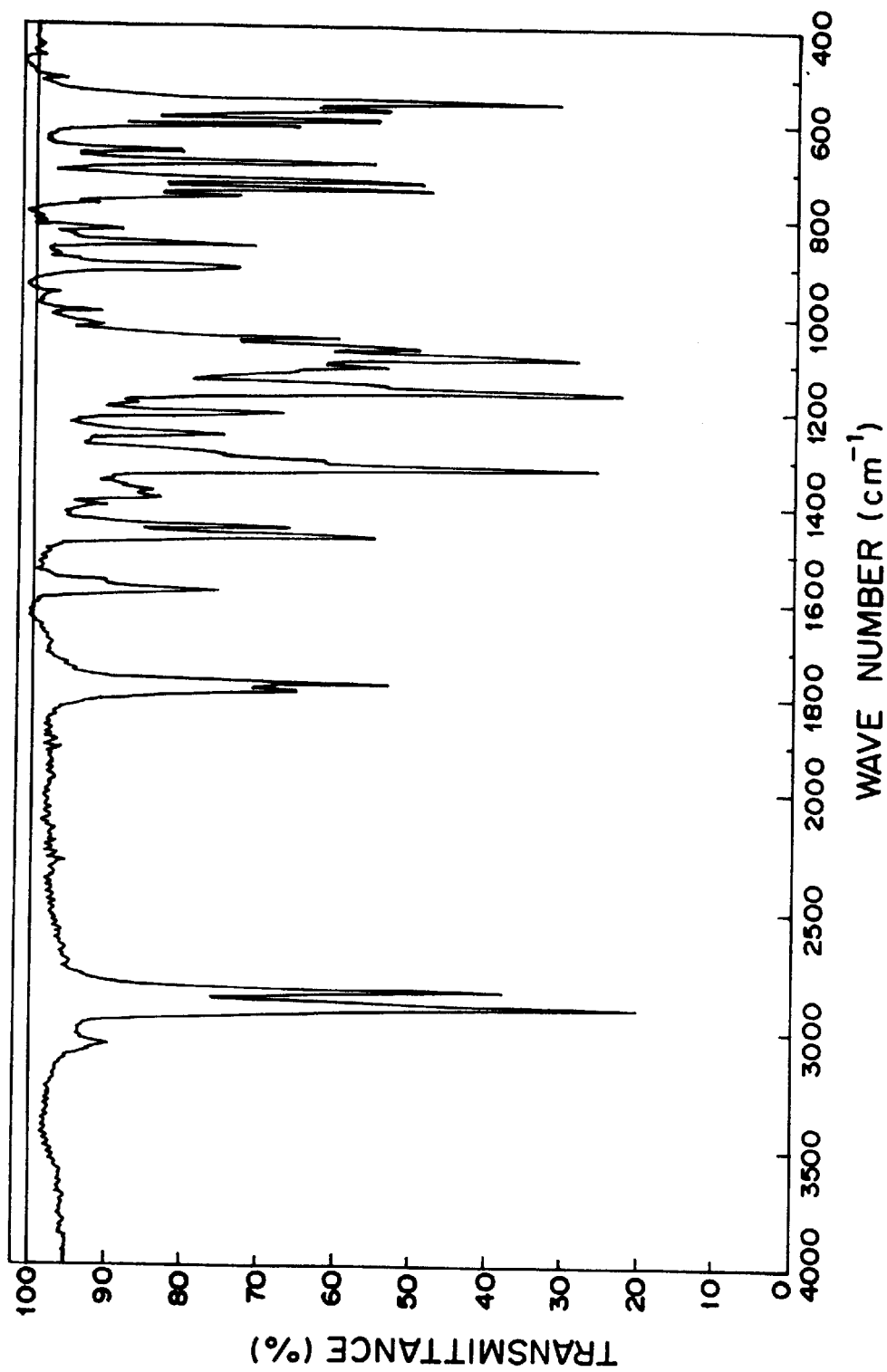
FIG. 14 shows an infrared-absorption spectrogram of the compound obtained in Working Example 14.

FIG. 14 shows an infrared-absorption spectrogram thereof.

(Working Example 15)

The operation was carried out in the same way as that of Working Example 13, except that 42.1 gr. of benzoyl chloride, and 34 gr. of pyridine used in Working Example 13 were replaced with 24 gr. of acethyl chloride and 38 gr. of triethylamine. As a result, 78 gr. of white crystalline powders having a melting point of 173° C. were obtained. From the results of IR-analysis, H-NMR analysis and elemental analysis (see Table 15) thereof, this product was identified as {2,4-bis(phenylsulfonyl)phenyl)acetate.

TABLE 15

| Elementary Analysis Values (%) | C | H | S |
|---|---|---|---|
| Found Values | 57.5 | 3.8 | 15.2 |
| Calculated Values (As $C_{20}H_{16}O_6S_2$) | 57.7 | 3.9 | 15.4 |

Figure 15:
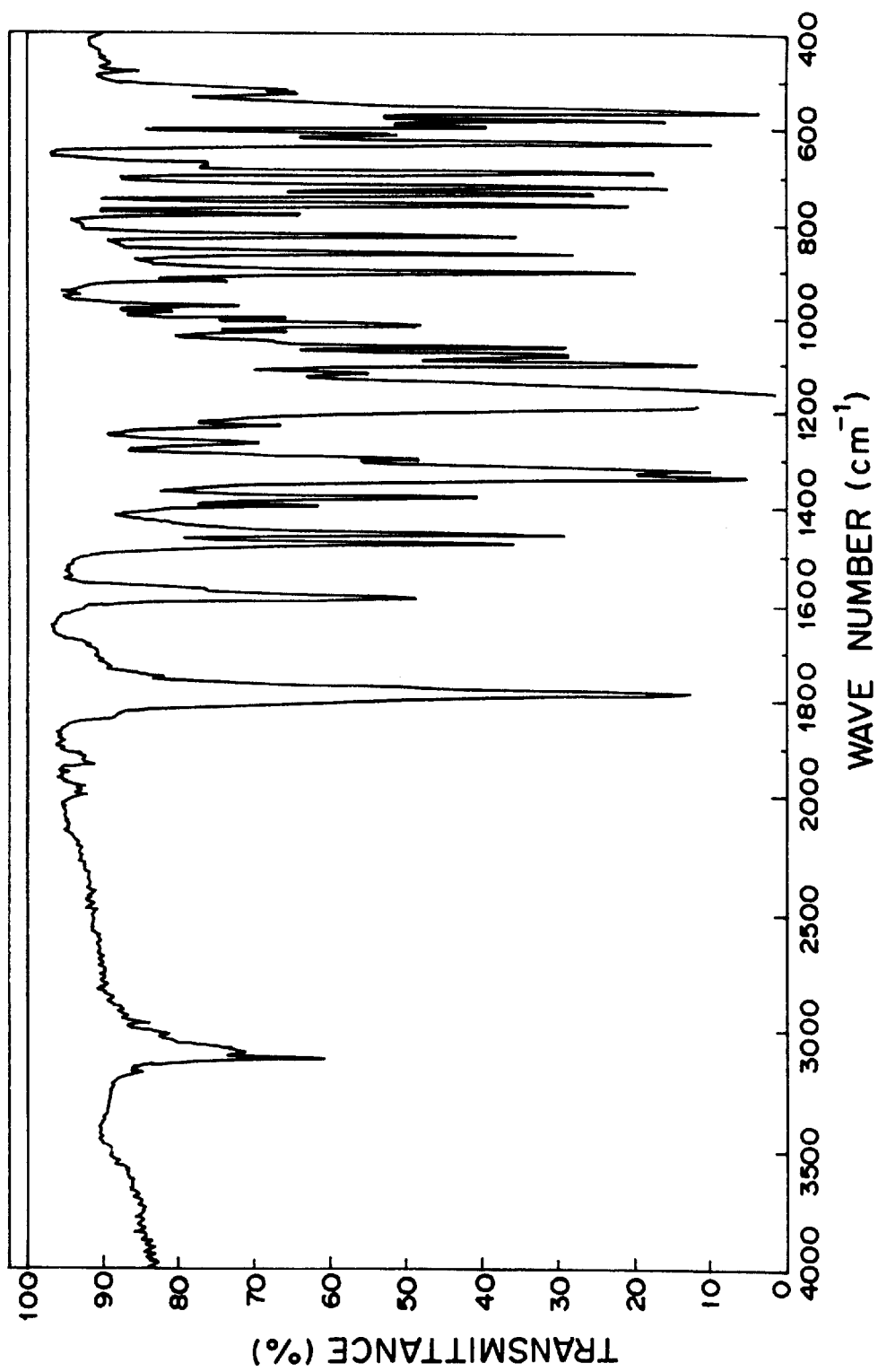
FIG. 15 shows an infrared-absorption spectrogram of the compound obtained in Working Example 15.

FIG. 15 shows an infrared-absorption spectrogram thereof.

(Working Example 16)

According to a recrystallization method, 48 gr. of a white crystalline powder having a melting point of 157° C. was obtained from 48.5 gr. of 2,4-bis(phenylsulfonyl)phenol, 1.5 gr. of {2,4-bis(phenylsulfonyl)phenyl} benzenesulfonate and 100 gr. of toluene. This product was identified as 2,4-bis(phenylsulfonyl)phenyl containing 1.2% of {2,4-bis(phenylsulfonyl)phenyl} benzenesulfonate from results of a high performance liquid chromatographic analysis. Hereafter, a composition obtained according to a recrystallization method will be hereinafter referred to as a "recrystallization method".

(Working Example 17)

49.5 gr. of 2,4-bis(phenylsulfonyl)phenol and 0.5 gr. of 1-methoxy-2,4-bis(phenylsulfonyl)benzene were mixed and melted, and crystallized at a temperature of 130° C. to 140° C., cooled to a room temperature, and pulverized so as to obtain 48.5 gr. of white crystalline powders having a melting point of 157° C. This product was identified as 2,4-bis-(phenylsulfonyl)phenol containing 1.5% of 1-methoxy-2,4-bis-(phenylsulfonyl)benzene from, results of a high performance liquid chromatographic analysis.

Incidentally, hereafter, a developer composition obtained according to the present method will be referred to as a "melt method".

(Working Example 18)

49.0 gr. of 2,4-bis(phenylsulfonyl)phenol and 1.0 gr. of {2,4-bis(phenylsulfonyl)phenylcarboxylate were dissolved in 100 gr. of toluene, and the solution was slowly dropped in 500 gr. of hexane while stirring and then, deposits were filtered and dried so as to obtain 48 gr. of white crystalline powders having a melting point of 158° C. This product was identified as 2,4-bis(phenylsulfonyl)phenol containing 1.5% of {2,4-bis(phenylsulfonyl)phenyl} phenylcaboxylate.

(Working Example 19)

Preparation of Basic Dye Dispersion 20 gr. of 3-N,N-dibutylamino-6-methyl-7-anilinofluoran was pulverized by using a ball mil in 80 gr. of an aqueous solution having a concentration of 5% of polyvinyl alcohol (PVA-117, the trade name of Kurare Co.) so as to prepare a dispersion of a basic dye having an average particle size of 0.6 μm.

Preparation of Sensitizing Agent Dispersion 20 gr. of 1,2-bis(3-methylphenoxy)ethane were pulverized by using a ball mil in 30 gr. of an aqueous solution having a concentration of 5% of polyvinyl alcohol (PVA-117), so as to prepare a dispersion of a sensitizing agent Having an average particle size of 0.6 μm.

Preparation of Developer Dispersion 20 gr. of 2,4-bis(phenylsulfonyl)phenol containing 1.2% of {2,4-bis(phenylsulfonyl)phenyl} benzenesulfonate was pulverized by using a ball mil in 30 gr. of an aqueous solution having a concentration of 5% of methylcellulose, so as to prepare a dispersion of a developer having an average particle size of 1.1 μm; the dispersion being preserved at a temperature of 40° C. for a period of 30 days so as to use as a developer dispersion.

Preparation of Pigment Dispersion 30 gr. of calcium carbonate (Uniba 70, the trade name of Shiraishi Kogyo Co.), 70 gr. of water and 0.4 gr. of an aqueous solution having a concentration of 10% of sodium hexametaphosphate were agitated by a homogenizer with a revolution speed of 15,000 rpm for a period of 15 minutes so as to prepare a pigment dispersion.

Preparation of Coating Liquid for Thermosensible Recording Layer 3 gr. of the above basic dye dispersion, 3 gr. of the above sensitizing agent dispersion, 3 gr. of the above developer dispersion, 7 gr. of the above pigment dispersion, and furthermore, 2.0 gr. of zinc stearate (HIDORIN Z-7, registered trademark of Chukyo Yushi Co.) having a concentration of 31%, 0.2 gr. of paraffin wax (HIDORIN P, registered trade name of Chukyo Yushi Co.) having a concentration of 31%, 6 gr. of an aqueous solution having a concentration of 5% of polyvinyl alcohol (PVA-117), and 9 gr. of water were mixed so as to obtain a coating liquid for a thermalsensitive recording layer.

Formation of Thermalsensitive Recording Paper

The coating liquid for a thermalsensitive recording layer was applied onto the surface of a paper-made base by using a wire bar so as to ensure the weight of the thermosensitive recording layer of 5 gr./m$^2$ after drying, and dried in an oven at a temperature of 60° C., and calendered to obtain a smoothness of 200 seconds (by Bekk Tester).

(Working Example 20 to 30)

The operation was carried out in the same way as that of Working Example 19. except that developers shown in Table 16 were used instead of 20 gr. of 2,4-bis(phenylsulfonyl)phenol containing 1.2% of {2,4-bis(phenylsulfonyl)phenyl} benzenesulfonate as a developer used in Working Example 19, and furthermore, in Working Examples 20, 27 and 28, polyvinylalcohol (PVA-117) was used as a dispersing agent for pulverizing the developer instead of methylcellulose used in Working Example 19. Used developers and the weights thereof will be shown in Table 16.

TABLE 16

| | Developers | Amount Used (gr) |
|---|---|---|
| Working Ex. 20 | 2,4-bis(phenylsulfonyl)phenol containing 1.5% of {2,4-bis(phenylsulfonyl)phenyl} phenylcarboxylate(, which is a composition used in Working Ex. 1) | 20 |
| Working Ex. 21 | 2,4-bis(phenylsulfonyl)phenol containing 1.0% of 1-methoxy-2,4-bis(phenylsulfonyl) benzene (by Dissolving method) | 20 |
| Working Ex. 22 | 2,4-bis(phenylsulfonyl)phenol containing 1.3% of 1-ethoxy-2,4-bis(phenylsulfonyl) benzene | 20 |
| Working Ex. 23 | 2,4-bis(phenylsulfonyl)phenol containing 3.0% of 1-iso-propoxy-2,4-bis-(phenylsulfonyl)benzene | 20 |
| Working Ex. 24 | 2,4-bis(phenylsulfonyl)phenol containing 0.5% of {2,4-bis(phenylsulfonyl)-benzenesulfonate and 1.0% of 1-ethoxy-2,4-bis(phenylsulfonyl) benzene | 20 |
| Working Ex. 25 | 2-(4-methylphenylsulfonyl)-4-(phenylsulfonyl)phenol containing 1.8% of {2-(4-methylphenylsulfonyl)-4-(phenylsulfonyl)benzenesulfonate | 20 |
| Working Ex. 26 | 2-(2,5-dimethylphenylsulfonyl)-4-(phenylsulfonyl)phenol containing 2.5% of 1-iso-propoxy-2-(2,5-dimethylphenylsulfonyl)-4-(phenylsulfonyl) benzene | 20 |
| Working Ex. 27 | 2,4-bis(phenylsulfonyl)-5-methylphenol containing 3.0% of 1- {2,4-bis-(phenylsulfonyl)-5-methylphenoxy} -2,3-epoxypropane | 20 |
| Working Ex. 28 | 2,4-bis(4-methylphenylsulfonyl)phenol containing 1.5% of {2,4-bis(4-methylphenylsulfonyl)phenyl} allyl ether | 20 |
| Working Ex. 29 | 2,4-bis(4-chlorophenylsulfonyl)phenol containing 2.2% of {2,4-bis(4-chlorophenylsulfonyl)phenyl} 4-chlorobenzenesulfonate | 20 |
| Working | 2,4-bis(3,4-dimethylphenylsulfonyl)phenol | 20 |

TABLE 16-continued

| | Developers | Amount Used (gr) |
|---|---|---|
| Ex. 30 | containing 0.9% of {2,4-bis(3,4-dimethylphenylsulfonyl)phenyl} phenylcarboxylate | |

In Table 16, developers used in Working Examples 22–30 were obtained by Recrystallization method.

(Working Example 31)

The operation was carried out in the same way as that of Working Example 19, except that 0.4 gr. of {2,4-bis(2,5-dimethylphenylsulfonyl)phenyl} 2,5-dimethylbenzenesulfonate and 19.6 gr. of 2,4-bis(2,5-dimethylphenylsulfonyl)phenol were used instead of 20 gr. of 2,4-bis(phenylsulfonyl)phenol containing {2,4-bis (phenylsulfonyl)phenyl} benzenesulfonate 1.2% of as a developer used in Working Example 19.

(Working Example 32)

Instead of 20 gr. of 2,4-bis(phenylsulfonyl)phenol containing 1.2% of {2,4-bis(phenylsulfonyl)phenyl}-benzenesulfonate as a developer used in Working Example 19, 10 gr. of {2,4-bis(phenylsulfonyl)-5-methylphenyl} phenylcarboxylate and 10 gr. of 2,4-bis(phenylsulfonyl)-5-methylphenol were used so as to prepare a developer dispersion. Furthermore, the operation was carried out in the same way as that of Working Example 19, except that this resultant dispersion was used in an amount of 6 gr., when an coating liquid for a thermalsensitive recording layer was prepared.

(Comparative Examples 1 and 2)

The operation was carried out in the same way as that of Working Example 19, except that the following developers were used instead of 20 gr. of 2,4-bis(phenylsulfonyl)phenol containing 1.2% of {2,4-bis(phenylsulfonyl)phenyl} benzenesulfonate as a developer used in Working Example 19.

| Comparative Example 1 | |
|---|---|
| 2,4-bis(phenylsulfonyl)phenol | 20 gr. |
| Comparative Example 2 | |
| 2(4-methylphenylsulfonyl)-4(phenylsulfonyl)phenol | 20 gr. |

Developer dispersions which were obtained in Working Examples 19 to 32 and Comparative Examples 1 and 2 were preserved at a temperature of 40° C. for a period of 30 days. As a result of the appearance observation of the dispersions by the naked eye, there was nothing wrong in Working Examples 19 to 32, while the dispersions in Comparative Examples 1 and 2 had been deteriorated, and particles therein had been precipitated on the lower layer and solidified.

(Comparative Example 3)

20 gr. of 2,2-bis(4-hydroxyphenyl)propane (disclosed in Japanese Patent Publication No.3-54655) was used instead of 20 gr. of 2,4-bis(phenylsulfonyl)phenol containing 1.2% of {2,4-bis(phenylsulfonyl)phenyl}-benzenesulfonate as a developer used in Working Example 19, Furthermore the operation was carried out in the same way as that of Working Example 19, except that a storage test of an aqueous slurry of the resultant developer at a temperature of 40° C. for a period of 30 days was omitted.

Then, an optical test of thermalsensitive recording papers which were obtained in Working Examples 19 to 32 and Comparative Examples 1 to 3 were carried out under copy mode conditions of a FUJITU Facsimile FF1700RX type machine. Furthermore, the following performance tests also were carried out. The result is shown in Table 19.

Performance Comparative Test

Optical Density: There were conducted measurements by using Macbeth densitometer.

Heat Resistance Test

Surface of the recording paper: The blushing on the surface after allowing the paper base to stand at a temperature of 60° C. for a period of 24 hours was observed with the naked eye by the following rating:

○: No change;

Δ: Slightly colored; and x: Colored.

Printing: Measure the percentage of the print density retention after 24 hours from printing at 60° C.

Print Density Retention (%)={(Print Density after 24 hrs)/(Density immediately after printing)}×100

Anti-Humidity Test

Surface of the recording paper: The blushing on the surface after allowing the paper base to stand in a humidity of 90% for a period of 24 hours was determined according to the rating of the blushing on surface in the test of heat resistance.

Printing: After allowing the printed paper to stand at a temperature of 40° C. in a humidity of 90% for a period of 24 hours, a retention percentage of the print density was determined according to the printing density test of heat resistance.

Anti-Plasticizer Test

The printing paper was wound around the outer surface of a glass bottle, wrapping the wound sheet with three layers of a wrap ("HIWRAP V-450" which is a registered trade mark of Mitsuitoatsu Chemical Co.) and allowed the bottle to stand at a temperature of 40° C. for a period of 2 hours, and then, a retention percentage of the print density was determined according to the measurement of the print density in the heat resistance test.

TABLE 17

| | | Heat Resistance Test | | Humidity Resistance Test | | Anti-Plasticizer Test |
|---|---|---|---|---|---|---|
| | Optical Density | Surface Blushing | Print Density Retention (%) | Surface Blushing | Print Density Retention (%) | Print Density Retention (%) |
| Working Example 19 | 1.36 | ○ | 99 | ○ | 99 | 90 |
| Working Example 20 | 1.36 | ○ | 99 | ○ | 99 | 90 |
| Working Example 21 | 1.36 | ○ | 99 | ○ | 99 | 90 |
| Working Example 22 | 1.36 | ○ | 99 | ○ | 99 | 90 |
| Working Example 23 | 1.36 | ○ | 99 | ○ | 99 | 90 |
| Working Example 24 | 1.36 | ○ | 99 | ○ | 99 | 90 |
| Working Example 25 | 1.36 | ○ | 99 | ○ | 99 | 91 |

TABLE 17-continued

| | | Heat Resistance Test | | Humidity Resistance Test | | Anti-Plasticizer Test |
|---|---|---|---|---|---|---|
| | Optical Density | Surface Blushing | Print Density Retention (%) | Surface Blushing | Print Density Retention (%) | Print Density Retention (%) |
| Working Example 26 | 1.35 | ○ | 99 | ○ | 99 | 91 |
| Working Example 27 | 1.30 | ○ | 90 | ○ | 94 | 75 |
| Working Example 28 | 1.32 | ○ | 94 | ○ | 96 | 70 |
| Working Example 29 | 1.31 | ○ | 93 | ○ | 96 | 81 |
| Working Example 30 | 1.34 | ○ | 95 | ○ | 97 | 80 |
| Working Example 31 | 1.33 | ○ | 95 | ○ | 97 | 80 |
| Working Example 32 | 1.33 | ○ | 91 | ○ | 95 | 75 |
| Comparative Example 1 ※ | | x | | | | |
| Comparative Example 2 ※ | | x | | | | |
| Comparative Example 3 | 1.29 | Δ | 63 | Δ | 65 | 10 |

※ In Comparative Examples 1 and 2, since the blushing on surface occurred at 60° C., other performance comparative tests was discontinued.

As apparent from the foregoing, the developer according to the present invention can resist a long-term storage without hydrating in the form of a aqueous slurry, and a thermalsensitive recording medium in which this developer composition is used, is excellent in, coloring property, and suffers a lower surface blushing with lapse of time, and is excellent in a storage stability of a recorded image, in particular, in heat resistance, humidity resistance and anti-plasticizer.

EFFECT OF THE INVENTION

According to the present invention, an aqueous slurry of the developer is excellent in a long-term storage stability without hydrating, and furthermore, a thermalsensitive recording medium in which this developer composition is used, can be provided, which is of high sensitivity and suffers a lower surface blushing with the lapse of time, and is excellent in a storage stability of a recorded image, in particular, in heat resistance, humidity resistance and anti-plasticizer.

We claim:

1. A thermalsensitive recording medium having a thermalsensitive recording layer mainly comprising a basic dye precursor, a developer and a sensitizing agent on the surface of a supporting base material, wherein a developer composition comprising at least one of sulfonyl compounds of the general formula (1),

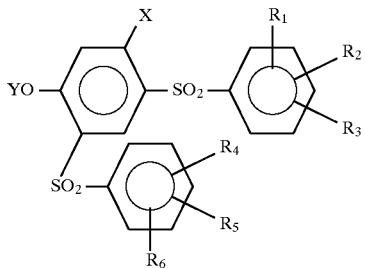 (1)

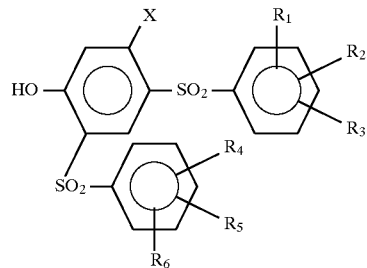 (2)

wherein X represents hydrogen atom or an alkyl group of 1~4 carbon atoms; $R_1$, $R_2$, $R_3$, $R_4$, $R_5$ and $R_6$ which may be the same or different, represent a hydrogen atom, a halogen atom or an alkyl group of 1~4 carbon atoms; and Y represents an alkyl group, an aralkyl group, an allyl group, a cyclohexyl group, an alkyl group-substituted or non-substituted aryl group, an alkylsulfonyl group, a benzenesulfonyl group, an alkylbenzenesulfonyl group, an alkyloyl group, a benzoyl group, an alkylbenzoyl group, an acryloyl group, a methacryloyl group or a glycidyl group; and at least one of sulfonyl compounds of general formula (2), wherein X, $R_1$, $R_2$, $R_3$, $R_4$, $R_5$ and $R_6$ are as defined in the above formula (1) is included in the above thermalsensitive recording layer.

2. The thermalsensitive recording medium according to claim 1 wherein said developer composition is included in the thermalsensitive recording layer in the incorporating rate of the sulfonyl compound represented by the general formula (1) to the sulfonyl compound represented by the general formula (2) is within a range of from 10 ppm to twofold by weight.

* * * * *